US006432096B1

(12) United States Patent
McFall et al.

(10) Patent No.: US 6,432,096 B1
(45) Date of Patent: Aug. 13, 2002

(54) ABSORBENT INTERLABIAL DEVICE HAVING AN INTEGRALLY FORMED TAB

(75) Inventors: Ron R. McFall, West Chester; Wilfried M. Kollner; Thomas W. Osborn, both of Cincinatti; Pamela J. Brown, Maineville; Lee M. Hines, Wyoming, all of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/674,473

(22) PCT Filed: Apr. 30, 1999

(86) PCT No.: PCT/US99/09596

§ 371 (c)(1),
(2), (4) Date: Nov. 1, 2000

(87) PCT Pub. No.: WO99/56689

PCT Pub. Date: Nov. 11, 1999

Related U.S. Application Data

(63) Continuation-in-part of application No. 09/266,639, filed on Mar. 11, 1999, which is a continuation-in-part of application No. 09/071,444, filed on May 1, 1998, now Pat. No. 6,183,456, which is a continuation-in-part of application No. 09/071,425, filed on May 1, 1998, now Pat. No. 6,270,486, which is a continuation-in-part of application No. 08/876,206, filed on Jun. 16, 1997, now abandoned.

(51) Int. Cl.$^7$ .......................... A61F 13/15; A61F 13/20
(52) U.S. Cl. .................... 604/385.17; 604/904
(58) Field of Search .................. 604/904, 385.17, 604/385.18

(56) References Cited

U.S. PATENT DOCUMENTS

| 4,248,822 A | 2/1981 | Schmidt |
| 4,533,357 A | 8/1985 | Hall |
| 5,336,208 A | 8/1994 | Rosenbluth et al. |
| 5,702,380 A | * 12/1997 | Walker .................. 604/385.17 |
| 5,762,644 A | * 6/1998 | Osborn, III et al. .... 604/385.17 |
| 5,891,126 A | * 4/1999 | Osborn, III et al. .... 604/385.17 |
| 5,928,452 A | * 7/1999 | McFall et al. ......... 604/385.17 |

* cited by examiner

Primary Examiner—Dennis Ruhl
(74) Attorney, Agent, or Firm—Matthew P. Fitzpatrick; Kevin C. Johnson; Roddy M. Bullock

(57) ABSTRACT

The present invention relates to absorbent devices such as sanitary napkins, pantiliners, interlabial devices, and incontinence devices. In a preferred embodiment, the present invention relates to an improved absorbent device that is insertable into the interlabial space of a female wearer for catamenial purposes (including menses and mid-cycle discharges), incontinence protection (including urine), or both. The absorbent interlabial device has at least on body-contacting surface and a backsheet having an integral protrusion formed therein of sufficient dimensions to aid in insertion into the interlabial space. An apparatus for forming the integral protrusion in the backsheet is disclosed. The apparatus comprises a female forming member having an opening therein, and a compression member having and opening therethough in operative aligned relationship with the opening of the female forming member. A male forming member having a male forming protrusion operatively disposed in aligned relationship with the opening of the female forming member and compression member, and moveable therethough can be urged through the openings. A method of making an integral protrusion in a backsheet is disclosed. The backsheet is compressed between the female forming member and the compression member. The backsheet has an uncompressed region coincident the aligned openings of the female forming member and the compression member. A male forming protrusion is urged through the aligned openings, thereby contacting and straining the backsheet material coincident said first and second openings to form a strain induced plastically deformed protrusion in the backsheet.

5 Claims, 7 Drawing Sheets

ABSORBENT INTERLABIAL DEVICE HAVING AN INTEGRALLY FORMED TAB

This application is a 35 USC 371 filing of PCT/US99/09596. This application is a continuation-in-part of application Ser. No. 09/266,639, filed Mar. 11, 1999, which is a continuation-in-part of application Ser. No. 09/071,444, filed May 1, 1998, and now U.S. Pat. No. 6,183,456. This application is also a continuation-in-part of application Ser. No. 09/071,425, filed May 1, 1998, and now U.S. Pat. No. 6,270,486, which is a continuation-in-part of application Ser. No. 08/876,206, filed Jun. 16, 1997, now abandoned.

FIELD OF THE INVENTION

This invention relates to absorbent articles or devices. In a preferred embodiment, the present invention relates to an improved absorbent device that is worn interlabially by female wearers for catamenial purposes, incontinence protection, or both.

BACKGROUND OF THE INVENTION

All manner and variety of absorbent articles configured for the absorption of body fluids such as menses, urine and feces are well known. With respect to feminine protection devices, the art has offered two basic types; sanitary napkins have been developed for external wear about the pudendal region while tampons have been developed for internal wear within the vaginal cavity for interruption of menstrual flow therefrom. Such tampon devices are disclosed in U.S. Pat. No. 4,412,833, entitled "Tampon Applicator", issued to Weigner, et al. on Nov. 1, 1983, and U.S. Pat. No. 4,413,986, entitled "Tampon Assembly With Means For Sterile Insertion", issued to Jacobs on Nov. 8, 1983.

Hybrid devices which attempt to merge the structural features of the sanitary napkins and the tampons into a single device have also been proposed. Such hybrid devices are disclosed in U.S. Pat. No. 2,092,346, entitled "Catamenial Pad", issued to Arone on Sep. 7, 1937, and U.S. Pat. No. 3,905,372, entitled "Feminine Hygiene Protective Shield", issued to Denkinger on Sep. 16, 1975. Other less intrusive hybrid devices are known as labial or interlabial sanitary napkins and are characterized by having a portion which at least partially resides within the wearer's vestibule and a portion which at least partially resides external of the wearer's vestibule. Such devices are disclosed in U.S. Pat. No. 2,662,527, entitled "Sanitary Pad", issued to Jacks on Dec. 15, 1953, and U.S. Pat. No. 4,631,062, entitled "Labial Sanitary Pad", issued to Lassen, et al. on Dec. 23, 1986.

Interlabial pads have the potential to provide even greater freedom from inconvenience because of their small size and reduced risk of leakage. Numerous attempts have been made in the past to produce absorbent devices which would combine the best features of tampons and sanitary napkins while avoiding at least some of the disadvantages associated with each of these types of devices. Examples of such devices are described in U.S. Pat. No. 2,917,049 issued to Delaney on Dec. 15, 1959, U.S. Pat. No. 3,420,235 issued to Harmon on Jan. 7, 1969, U.S. Pat. No. 4,595,392 issued to Johnson, et al. on Jun. 17, 1986, and U.S. Pat. No. 5,484,429 issued to Vukos, et al. on Jan. 16, 1996. A commercially available interlabial device is the INSYNC MINIFORM interlabial pad which is marketed by A-Fem of Portland, Oreg. and described in U.S. Pat. Nos. 3,983,873 and 4,175,561 issued to Hirschman on Oct. 5, 1976 and Nov. 27, 1979, respectively.

Many of these devices have not met with great commercial success, however. There are drawbacks associated with all of the above products. For example, the device described in the Delaney patent does not appear to be capable of an easy and comfortable insertion, due to the possibility of the layers of absorbent material opening up during insertion. The commercially available IN-SYNC interlabial device suffers from the disadvantage that it may tend to allow by-pass flow around its edges. Such flow can cause body soiling or panty soiling which many consumers find unacceptable. Additionally, previously known interlabial devices such as the INSYNC Minifonn interlabial pad may not reliably cover the urethra and/or the vaginal introitus during all body movements (e.g. when the wearer is squatting). Such products may also not be reliably expelled when the wearer urinates. Further, such an interlabial pad may not have sufficient absorbent capacity for use during a wearer's menstrual period, and/or may fall out of the interlabial space when fully loaded. In order to handle the wearer's menstrual flow, a user may have to wear the interlabial pad in combination with a sanitary napkin.

Another factor affecting commercial success is the ease of use, including insertion and removal of the device. Typically, the user grasps the device with her fingers and inserts it in position. The user may also need to grasp the device for removal, particularly if it is not expelled during urination. For either insertion or removal, it is desirable that the user not touch the body-facing portion of the device. Thus, for ease of insertion and/or removal, a grasping tab or other gripping surface is very beneficial. However, providing such tabs or surfaces adds to the number of separate elements of the article, thereby increasing manufacturing complexity, and ultimately the cost of the device.

Therefore, a need exists for an improved interlabial device which will facilitate insertion and/or removal of the device. Such a device should also be easy to insert and/or remove, and be comfortable during wear. A need exists for an interlabial device which also covers the walls of the wearer's labia throughout a range of body motions and reliably covers the vaginal introitus and preferably also the urethra during such motions. A need also exists for an improved interlabial device which has sufficient capacity to serve as a stand alone protection function during the heavy flow days of a wearer's menstrual period. A need also exists for an improved absorbent interlabial device which is economical to produce in commercial quantities. A need also exists for an improved absorbent interlabial device which may be used as part of a system of feminine hygiene protection or with a feminine hygiene kit.

SUMMARY OF THE INVENTION

The present invention relates to absorbent devices such as sanitary napkins, pantiliners, interlabial devices, and incontinence devices. In a preferred embodiment, the present invention relates to an improved absorbent device that is insertable into the interlabial space of a female wearer for catamenial purposes (including menses and mid-cycle discharges), incontinence protection (including urine), or both. The absorbent interlabial device has at least one body-contacting surface and a backsheet having an integral protrusion formed therein of sufficient dimensions to aid in insertion into the interlabial space.

An apparatus for forming the integral protrusion in the backsheet is disclosed. The apparatus comprises a female forming member having an opening therein, and a compression member having an opening therethrough in operative aligned relationship with the opening of the female forming member. A male forming member having a male forming protrusion operatively disposed in aligned relationship with the openings of the female forming member and compression member, and moveable therethrough can be urged through the openings.

A method of making an integral protrusion in a backsheet is disclosed. The backsheet is compressed between the female forming member and the compression member. The backsheet has an uncompressed region coincident the aligned openings of the female forming member and the compression member. A male forming protrusion is urged through the aligned openings, thereby contacting and straining the backsheet material coincident said first and second openings to form a strain induced plastically deformed protrusion in the backsheet.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF THE INVENTION

Figure 1:
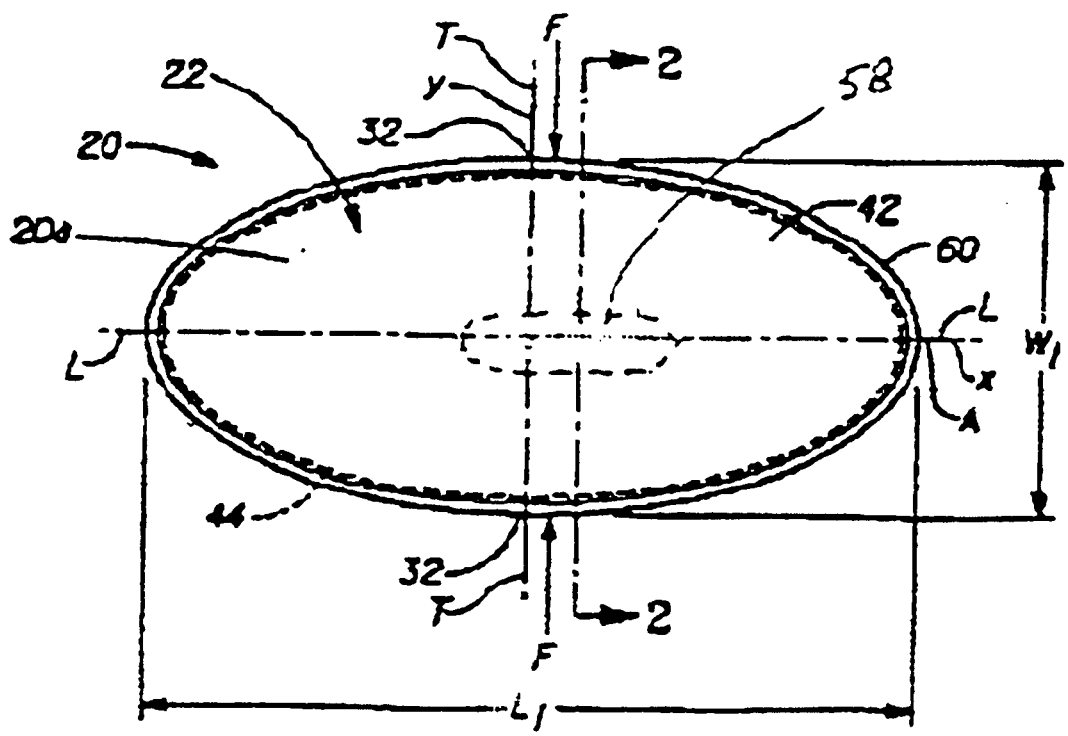
FIG. 1 is a top plan view of a preferred embodiment of the absorbent interlabial device according to the present invention.
Figure 2:
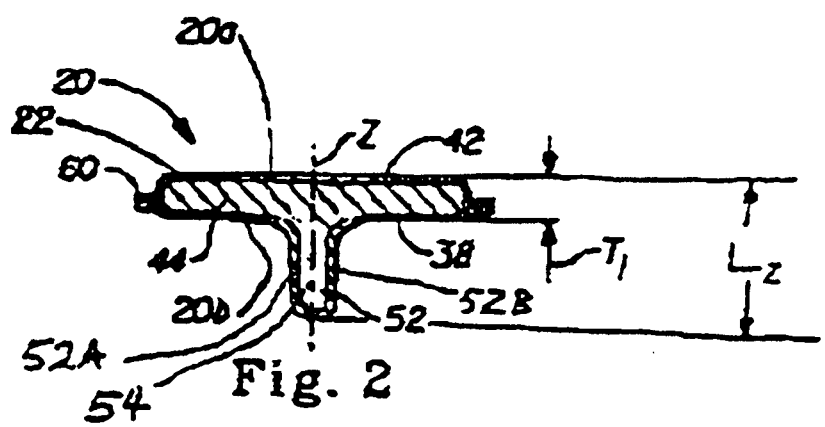
FIG. 2 is a cross sectional view of the absorbent interlabial device shown in FIG. 1, taken along line 2—2 of FIG. 1.
Figure 3:
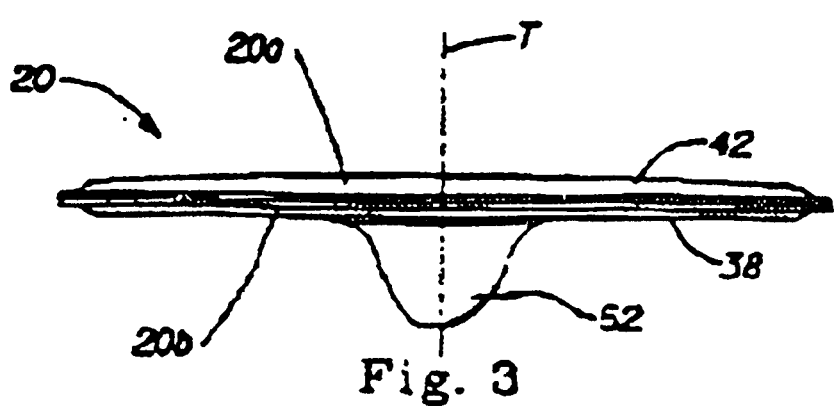
FIG. 3 is a side view of the absorbent interlabial device shown in FIG. 1.

The present invention is directed to absorbent articles or devices. In a preferred embodiment, the present invention relates to an absorbent interlabial device. The absorbent interlabial device has at least one body-contacting surface which can comprise a substance that contacts the wearer's body for assisting the interlabial device in staying in place in the desired position in the interlabial space. FIGS. 1–3 show one embodiment of an absorbent interlabial device, interlabial device 20. The present invention, however, is not limited to a structure having the particular configuration shown in the drawings.

As used herein, the term "absorbent interlabial device" refers to a structure which has at least some absorbent components, and which is specifically configured to reside at least partially within the interlabial space of a female wearer during use. Preferably, when the absorbent interlabial device 20 is properly sized for an individual wearer, more than half of the entire absorbent interlabial device 20 of the present invention resides within such interlabial space. More preferably, substantially the entire absorbent interlabial device 20 resides within such interlabial space, and most preferably the entire absorbent interlabial device 20 resides within such interlabial space of a female wearer during use.

As used herein, the term "interlabial space" refers to that space in the pudendal region of the female anatomy which is located between the inside surfaces of the labia majora extending into the vestibule. Located within this interlabial space are the labia minor, the vestibule and the principal urogenital members including the clitoris, the orifice of the urethra, and the orifice of the vagina. Standard medical authorities teach that the vestibule refers to the space bounded laterally by the inside surfaces of the labia minora and extending interiorly to the floor between the clitoris and the orifice of the vagina. Therefore, it will be recognized that the interlabial space as defined above may refer to the space between the inside surfaces of the labia majora, including the space between the inside surfaces of the labia minora also known as the vestibule. The interlabial space for purposes of the present description does not extend substantially beyond the orifice of the vagina into the vaginal interior.

The term "labia" as used herein refers generally to both the labia majora and labia minora. The labia terminate anteriorly and posteriorly at the anterior commissure and the posterior commissure, respectively. It will be recognized by those skilled in the art that there is a wide range of variation among women with respect to the relative size and shape of labia majora and labia minora. For purposes of the present description, however, such differences need not be specifically addressed. It will be recognized that the disposition of the absorbent interlabial device into the interlabial space of a wearer as defined above will require placement between the inside surfaces of the labia majora without regard to the precise location of the boundary between the labia majora and the labia minora for a particular wearer. For a more detailed description of this portion of the female anatomy, attention is directed to *Gray's Anatomy*, Running Press 1901 Ed. (1974), at 1025–1027.

The absorbent interlabial device 20 shown in FIG. 1 has a longitudinal centerline L which runs along the "x" axis. The term "longitudinal", as used herein, refers to a line, axis or direction in the plane of the interlabial device 20 that is generally aligned with (e.g., approximately parallel to) a vertical plane which bisects a standing wearer into left and right body halves when the interlabial device 20 is worn. The terms "transverse," "lateral," or "y direction" as used herein, are interchangeable, and refer to a line, axis, or direction that is generally perpendicular to the longitudinal direction. The lateral direction is shown in FIG. 1 as the "y" direction. The absorbent interlabial device 20 shown in FIG. 1 also has a transverse centerline T. The "z" direction, shown in FIG. 2, is a direction parallel to the vertical plane described above. The term "upper" refers to an orientation in the z-direction toward the wearer's head. "Lower" or downwardly is toward the wearer's feet.

The interlabial device 20 shown in FIGS. 1–3 is in one preferred configuration. The interlabial device 20 has a body-facing (or "body-contacting" side) 20A and an opposed underside 20B. The interlabial device comprises a pad-like main body portion (or "central absorbent portion") 22 and a placement and removal tab 52, which is an integrally formed protrusion in the backsheet 38, to provide the overall interlabial device that can have a "T"-shaped cross-sectional configuration. As used herein, the term "integrally formed" with respect to tab 52 means formed as one piece with, i.e., without the addition of separate elements or materials. Likewise, as used herein with respect to tab 52, the term "integral with" means unitary, i.e., one piece with backsheet 38 as disclosed in detail herein. Thus, when formed by the method of the present invention, tab 52 is made by forming, reforming, or deforming a portion of backsheet 38, to form a protrusion such that the tab and at least a portion of the backsheet are the same material. Said differently, the term "integral with" with reference to tab 52 does not encompass separately joined elements, such as a discrete tab joined to the backsheet by melt fusion, adhesion, or other joining means.

The main body portion 22 can be in any suitable configuration. Non-limiting examples of shapes for the main body portion 22 when viewed from the top as in FIG. 1 include ovoid, elliptical, trapezoidal, rectangular, triangular, diamond-shaped, or any combination of the above. As shown in FIG. 1, the preferred plan view shape for the main body portion 22 and the overall absorbent interlabial device 20 is generally ovoid or elliptical. The plan view shape of the main body portion 22 tapers from the transverse centerline T towards its front and rear ends. The main body portion 22, in this embodiment, is relatively flat in its side profile, but may taper slightly from front to rear as shown in FIG. 3.

As shown in FIGS. 1–2, the interlabial device preferably comprises a liquid pervious topsheet 42, a liquid impervious backsheet 38 joined to the topsheet 42, and an absorbent core 44 positioned between the topsheet 42 and the backsheet 38. The interlabial device 20 is preferably of a size and shape that allows at least the majority of the device 20 to fit comfortably within the wearer's interlabial space and to cover the wearer's vaginal orifice, and preferably also the wearer's urethra. The interlabial device 20 at least partially blocks, and more preferably completely blocks and intercepts the flow of menses, urine, and other bodily exudates from the wearer's vaginal orifice and urethra.

As shown in FIGS. 2–3, the interlabial device comprises a tab 52 integrally formed with as a protrusion of a portion of backsheet 38. Tab 52 may be integrally formed with the entire backsheet as shown in cross section in FIG. 2. However, in the instance where the backsheet may itself be formed of two or more materials, it is only necessary for the present invention that the tab 52 be formed integral with the portion of the backsheet 38 in the region formed into a protrusion by the method of the present invention. Thus, for example, it may be beneficial to have the portion of the backsheet 38 at seam 60 to be a different material than at tab 52 to provide a softness benefit to the user. The presence of such a material would not change the essential characteristic that the tab 52 be integral with the remaining portion of the backsheet.

Tab 52 can be formed by forming, e.g., injection or blow molding a polymer film; reforming, e.g., heating and forming a thermoplastic film backsheet about a positive or negative mold surface; or deforming, e.g., strain induced plastic deformation. In a preferred method and apparatus, backsheet 38 is plastically deformed generally parallel to the Z-axis to form a permanent protrusion or tab 52. In a preferred embodiment, tab 52 is disposed generally centrally with respect to both the x and y axes. When disposed centrally, tab 52 can be symmetrical about both the L and T centerlines, which is the currently preferred configuration.

Tab 52 has sufficient dimensions to aid in insertion into the interlabial space of the user. By "sufficient dimensions" is meant that tab 52 can be gripped between the forefinger and thumb of the user while maintaining control of the device during insertion into the interlabial space. For example, tab 52 has a length L2 sufficient to form a gripping surface for the user's fingers. In a one embodiment length L2 is at least equal to distance T1 as shown in FIG. 2 and disclosed below. Length L2 can be at least about 10 m, and is more preferably at least about 15 mm. The maximum length L2 is limited only by the stress-strain properties of the backsheet material, but it is believed that at distances greater than about 40 mm, the tab 52 interferes with the proper use of the device, as well as the user's comfort. The dimension of tab 52 as measured parallel to the longitudinal axis L also be at least about 5 mm, and is more preferably at least about 15 mm and less than about 30. In one embodiment, the maximum dimension parallel to the longitudinal axis L is 25 mm and the length L2 is 15 mm, with the overall shape of the keel being generally semi-circular, as shown in FIG. 3. The overall dimension of the width of the keel, that is the dimension generally parallel to transverse axis T can be as little as twice the thickness of the backsheet material, but is preferably at least about 1 mm, and more preferably at least about 2 mm. Tab 52 may also be profiled so that it has a thickness or caliper differential from the proximal portion to the distal portion. In other words, the thickness can vary from thicker at the proximal end to thinner at the distal end, or vice versa.

Tab 52 comprises two sidewall portions 52A and 52B, which can be generally parallel for much of their length, as shown in FIG. 2. The two sidewalls join at the lowermost portion of tab 52 and define an interior portion 54. Interior portion may be substantially empty, that is, it may contain only air, or the sidewall portions may be substantially in contact with one another. In a preferred embodiment interior portion 54 comprises absorbent material, and may contain some material displaced from absorbent core 44 during the tab-forming process. Absorbent material disposed in interior portion 54 increases the absorptive capacity of the absorbent device, as well as aiding in keeping absorbed fluids away from the users body surface. In one embodiment, interior portion comprises absorbent gels or foams that expand when wet, thereby further increasing the absorbent capacity of the device.

Figure 5:
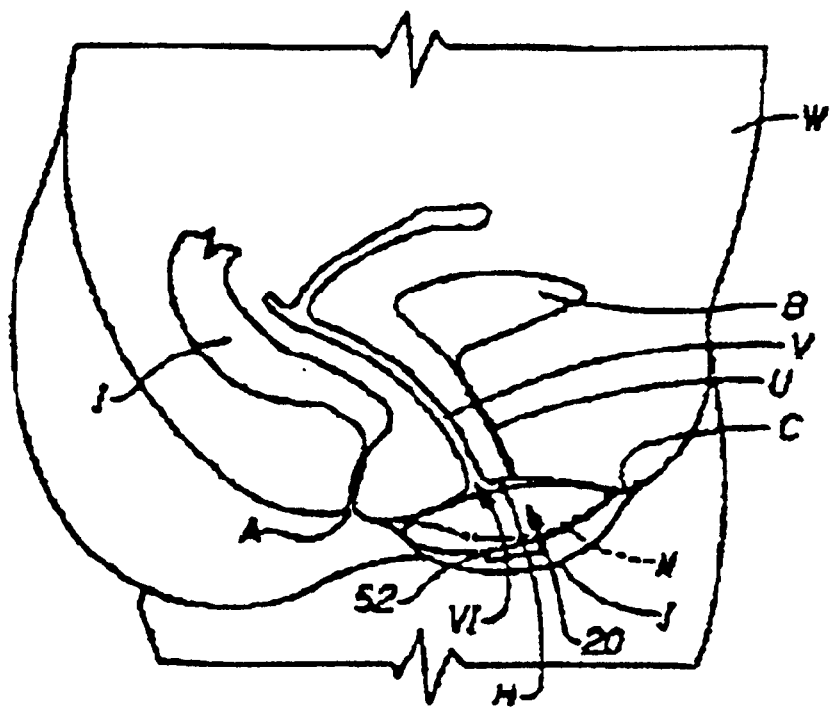
FIG. 5 is a cross-sectional saggital view of a human female wearer showing the placement of the absorbent interlabial device in the wearer's interlabial space.

As shown in FIGS. 2 and 3, tab 52 is preferably formed in shapes having rounded contours, such as being generally semi-circular or parabolic in shape. While it is recognized that shapes having sharp angles, such as rectangles, can be formed, as shown in FIG. 5, for purposes of permitting commercial production, rounded contours are currently preferred. Thus, when formed by the method of the present invention, tabs 52 having generally rounded contours can be reliably formed at relatively high speeds in line with existing production equipment, which decreases production costs, and ultimately decreases the cost to the consumer.

Therefore, unlike tabs that are added as a separate member and joined to the backsheet, the tab 52 of the present invention adds no material costs to the device, and eliminates the added processing complexity of joining parts, with the accompanying cost, quality and reliability issues.

The size of the interlabial device 20 is important to its comfort and effectiveness. The length of the absorbent interlabial device 20 is measured along the longitudinal centerline L in the longitudinal direction (or "x"-direction). The absorbent interlabial device 20 preferably has a length L, which is greater than about 60 mm and less than about 130 mm. More preferably, the length $L_1$ is between about 75 mm and about 105 mm. The width of the interlabial device 20 is measured along the transverse centerline T in the transverse direction (or "y"-direction). The absorbent interlabial device 20 preferably has a width $W_1$ which is between about 25 mm and about 50 mm. The thickness (or caliper) is the "Z"-direction dimension of the device 20. Caliper measurements given herein were measured using an AMES gauge with a 0.25 psi (1.7 kPa) (gauge) load and a 0.96 inch (2.44 cm) diameter foot. Those skilled in the art will recognize that if a 0.96 inch (2.44 cm) diameter foot is not appropriate for a particular sample size, the foot size may be varied while the load on the gauge is accordingly varied to maintain a confining pressure of 0.25 psi (1.7 kPa) (gauge). The caliper $T_1$ of the absorbent interlabial device 20 is preferably less than the width $W_1$ and the length $L_1$ of the device 20. Preferably, the caliper $T_1$ of the absorbent interlabial device 20 is less than or equal to about 8 mm, more preferably the caliper $T_1$ is less than or equal to about 6 mm, and even more preferably the caliper is less than or equal to about 4 mm.

Construction of the absorbent interlabial device 20 according to the particular size parameters given above results in a product with increased comfort and effectiveness compared to previous interlabial devices. For example, many women find interlabial pads which are shorter than the absorbent interlabial device 20 of the present invention to be difficult to position properly within the interlabial space. Even if such pads are positioned properly, they have an increased tendency to allow by-pass flow of body exudates around the edges of the pad. Additionally, many previous interlabial devices were not equipped with a liquid impervious backsheet having an integrally formed tab. These devices, therefore could allow body and panty soiling as a result of contact with the bottom surface of the device, and were relatively difficult to insert and/or remove.

The interlabial device 20 is preferably provided with sufficient absorbency to absorb and retain the exudates discharged from the wearer's body. The capacity of the product, however, is dependent at least partially upon the physical volume of the absorbent interlabial device 20, including any capacity afforded by the interior portion 54 of tab 52. The absorbent interlabial device preferably has a capacity of at least about 1 g of 0.9% by weight saline solution, and may have a capacity of up to about 30 g by using absorbent gels or foams that expand when wet. Preferably, capacities typically range from about 2 to about 12 grams, for saline. More preferably, the capacity of the device 20 is greater than or equal to about 6 g for saline. Those skilled in the art will recognize that the capacity for absorption of body exudates such as menses will typically be smaller than the capacities given above for absorption of saline. A method for measuring absorbent capacity is described in the Test Methods section, below. Since the interlabial space can expand, larger volumes can be stored in the interlabial space, particularly if the fluid is stored as a gel, which adjusts to the body pressures. Additionally, if the absorbent interlabial device 20 does not reside completely within the wearer's interlabial space, some of the absorbed exudates may be stored externally to the wearer's interlabial space.

The individual components which may be suitable for the various embodiments of the interlabial device 20 of the present invention will now be looked at in greater detail with reference to FIGS. 1–3.

The topsheet 42 comprises a first liquid pervious component. The topsheet 42 should be compliant, soft feeling, and non-irritating to the wearer's skin. Further, the topsheet 42 is liquid pervious permitting liquids (e.g., menses and/or urine) to readily penetrate through its thickness. A suitable topsheet 42 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, rayon, polypropylene, or polyethylene fibers) or from a combination of natural and synthetic fibers.

One suitable topsheet 42 for use in the present invention is a nonwoven material used as an overwrap for TAMPAX tampons which is made of starch bonded rayon fibers, and is obtained from Veratec of Walpole, Mass. A suitable topsheet may have a basis weight of about 18 g/m². This material is particularly suitable for use as a topsheet 42 because it is a biodegradable material.

As used herein, the term "biodegradable materials" refers to materials having greater than or equal to about 70% biodegradation (percentage of theoretical carbon dioxide evolution) after 28 days when measured according to the Sturm Test which has been designated Method 301B by the Organization for Economic Cooperation and Development, 2 rue Andre Pascal, 75775 Paris Cedex 16, France. Preferably, the materials comprising the interlabial device of the present invention have a biodegradation of greater than about 80% and, more preferably, biodegradation is greater than or equal to about 90%.

Another suitable type of topsheet 42 comprises an apertured formed film. Apertured formed films are pervious to body exudates and, if properly apertured, have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; U.S. Pat. No. 4,637,819 entitled "Macroscopically Expanded Three-Dimensional Polymeric Web for Transmitting Both Dynamically Deposited and Statically Contacted Fluids From One Surface to the Other", which issued to Ouellette, et al. on Jan. 20, 1987; U.S. Pat. Nos. 4,609,518 and 4,629,643 both issued to Curro, et al. on Sep. 2, 1986 and Dec. 16, 1986, respectively; U.S. Pat. No. 5,006,394 entitled "Multilayer Polymeric Film" issued to Baird on Apr. 9, 1991; and U.S. patent application Ser. No. 08/442,935 entitled "Fluid Transport Webs Exhibiting Surface Energy Gradients" filed in the name of Ouellette, et al. on May 31, 1995 (PCT Publication WO 96/00548, published Jan. 11, 1996). A preferred formed film topsheet for the present invention is the formed film described in one or more of the above patents and marketed on sanitary napkins by The Procter & Gamble Company of Cincinnati, Ohio as the "DRI-WEAVE" topsheet.

In embodiments in which the topsheet is an apertured film, the body surface of apertured film topsheet is preferably hydrophilic to help liquids transfer through the topsheet 42 faster than if the body surface was not hydrophilic. This diminishes the likelihood that body fluids will flow off the topsheet 42 instead of flowing into and being absorbed by the absorbent core 44. The body surface of the topsheet 42 can be made hydrophilic by treating it with a surfactant such as is described in U.S. Pat. No. 4,950,254 issued to Osborn, III. In a preferred embodiment, the surfactant is incorporated into the polymeric materials of the formed film topsheet.

The inner surface of topsheet 42 may be secured in contacting relation with an underlying absorbent layer. This contacting relationship results in liquid penetrating topsheet 42 faster. The topsheet 42 may be kept in a contacting relationship with an underlying layer by bonding the topsheet 42 to the underlying layer. However, it is not absolutely necessary to bond the face of the topsheet 42 to the face of the underlying layer. The topsheet 42 can be maintained in contact with an underlying absorbent component by entangling the fibers of the underlying layer with the topsheet, by fusing the topsheet 42 to an underlying absorbent layer by a plurality of discrete individual fusion bonds, or by any other means known in the art. The topsheet can also be maintained in contact with the underlying absorbent material due to the application of the pressure of the body against the body-contacting surface of the interlabial device.

It is not necessary that the topsheet 42 comprise a layer or material which is separate or distinct from the absorbent core 44. The topsheet 42 and absorbent core 44 may consist of one unitary structure in which the body-contacting surface of the absorbent core 44 will serve as the liquid pervious topsheet 42. In such an embodiment, the liquid pervious body-contacting surface may be hydrophilic or even hydrophobic so long as fluids readily penetrate through the surface and into the interior of the absorbent core 44. Additionally, such a unitary topsheet 42 and absorbent core 44 may be provided with a pore size gradient, capillary gradient, or hydrophilicity gradient, or any combination thereof, to assist in the absorption and retention of fluids in the interior of the absorbent core 44.

The absorbent core 44, which is best seen in FIG. 2, is positioned between the topsheet 42 and the backsheet 38. The absorbent core 44 provides the means for absorbing exudates such as menses and other body fluids. The absorbent core 44 preferably is generally compressible, conformable, and non-irritating to the user's skin. Preferably, the absorbent core 44 has the same general shape as the overall absorbent interlabial device 20.

The absorbent core 44 may comprise any suitable material that is capable of absorbing and/or retaining liquids (e.g. menses and/or urine). The absorbent core 44 be manufactured from a wide variety of liquid-absorbent materials commonly used in absorbent articles such as comminuted wood pulp which is generally referred to as airfelt. Examples of other suitable absorbent materials include cotton fibers or cotton lintels, creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers (in fibrous and particulate form); absorbent gelling materials; or any equivalent material or combinations of materials, or mixtures of these. Preferred absorbent materials comprise folded tissues, cotton batts, woven materials, nonwoven webs, rayon including needle punched rayon, and thin layers of foam. The absorbent core 44 may comprise a single material or a combination of materials.

A preferred material for the absorbent core 44 is batt of rayon or a rayon/cotton blend. In one particularly preferred embodiment, the absorbent core 44 is a batt which comprises a 50%/50% blend of baled bleached cotton fibers and baled rayon fibers. A tri-lobal rayon known as GALAXY rayon available from Courtaulds Fibers, Inc. of Axis, Ala. has been found to work well for the material comprising the absorbent core 44.

In other embodiments, the absorbent core 44 may consist of multiple independent layers of the same, or different materials (such as layers of absorbent materials with different absorbent properties), that are easily separable so the various layers can separate for disposal.

When the tab 52 is formed by the method of the present invention, absorbent core 44 may have a region of lower density 58 (shown in FIG. 1), which may in some embodiments be characterized as an opening, generally coincident with the area overlying tab 52. This is because, as detailed below, in one aspect of the method of the present invention, the absorbent core 44 can be positioned upon backsheet 38 prior to a mechanical forming protrusion being pressed through the absorbent core 44 and into backsheet 38 to form tab 52. To the extent that the absorbent core is itself formable or deformable, a certain amount of the absorbent core may be displaced, severed, or otherwise disrupted in the region coincident tab 52, thereby forming a localized region of lower density 58 in the absorbent core 44. This lower density region 58 can also be characterized by fibers of the absorbent core 44 being preferentially oriented toward the interior portion 54 of tab 52, thus providing for a beneficial fluid flow path into the interior portion 54.

The backsheet 38, which is best shown in FIGS. 2 and 3, prevents the exudates absorbed and contained in the absorbent core 44 from wetting articles and/or body parts which may contact the absorbent interlabial device 20 such as pants, pajamas, undergarments, pubic hair, the wearer's thighs, etc. The backsheet 38 should be flexible and impervious to liquids (e.g., menses and/or urine). As used herein, the term "flexible" refers to materials which are compliant and will readily conform to the general shape and contours of the human body. The backsheet 38 also provides protection for the wearer's fingers as the absorbent interlabial device 20 is inserted, or as the device is optionally removed with the fingers. Additionally, for a commercially-viable device of the present invention, the backsheet 38 should be plastically deformable, such that tab 52 can be formed by straining the backsheet material a sufficient amount to form a protrusion and induce a permanent set. Preferred materials for backsheet 38 include materials that can withstand high rates of strain such that devices 20 of the present invention can be produced at relatively high speeds.

The backsheet 38 may comprise plastically deformable woven or nonwoven materials, polymeric films such as thermoplastic films of polyethylene or polypropylene, composite materials such as a film-coated nonwoven material, or organic material such as a collagen film. Other suitable materials include biodegradable polymers that can be made into films and the like. Suitable biodegradable polymers include BIONELLE 3001 obtained from Showa Hugh Polymer Co. of Tokyo, Japan, and Matter Bi ZF03U-A obtained from Bicorp Co., distributor for Novamont S.P.A. of Rome, Italy and Biopol biodegradable polymer obtained from Monsanto, and Nordenia biodegradable polyester based film obtained from M&W Verpackungen GmBH, Germany . In one embodiment, the backsheet may be made from a polyethylene film having a thickness of from about 0.012 mm (0.5 mil) to about 0.051 mm (2.0 mils). An exemplary polyethylene film is manufactured by Clopay Corporation of Cincinnati, Ohio, under the designation P18-0401. Preferably, however, the backsheet comprises a film having a similar thickness, only which is made of biodegradable material, such as one of the biodegradable polymers described above.

The backsheet may also permit vapors to escape from the interlabial device 20 (i.e., be breathable) while still preventing exudates from passing through the backsheet. A suitable breathable backsheet material is a laminate of an apertured film such as that described in U.S. Pat. No. 3,929,135 issued to Thompson which is inverted so that the smaller openings of the tapered capillaries face the absorbent core 44 which is adhesively laminated to a microporous film such as that described in Exxon's U.S. Pat. No. 4,777,073.

In preferred embodiments, the backsheet 38 is dispersible and/or dissolvable in water. Polyvinyl alcohol (including co-polymers of polyvinyl alcohol) has been found to be suitable as a material for a dissolvable backsheet 38. The polyvinyl alcohol may be coated on a tissue, a nonwoven material such as a biodegradable nonwoven material (e.g. rayon), or coated with a wax, such as paraffin, or other hydrophobic coating to reduce the rate at which it dissolves in water. This allows the backsheet 38 to maintain its integrity during use, while retaining the ability to dissolve in water during disposal of the interlabial device 20.

The term "dispersible", as applied herein to an absorbent interlabial device or a component thereof, refers to an article or material which will disperse into at least two fragments in mildly agitated water. Such a device will break into pieces in a conventional toilet and/or domestic plumbing system, and will ultimately be effectively processed though a sewage treatment system. The term "dissolvable", as applied herein to an absorbent interlabial device or a component thereof, refers to an article or material which will at least partially dissolve and essentially assume liquid form or otherwise be indistinguishable to the naked eye from the liquid medium in which it is dissolved.

The components of the absorbent interlabial device 20 described above (topsheet 42, backsheet 38 having an integrally-formed tab 52, and absorbent core 44) can be assembled in any suitable manner. In the preferred embodiment shown in FIGS. 1–3, the components of the main body portion 22 are assembled in a "sandwich" configuration with the components sized so that the edges of the topsheet 42 and backsheet 38 extend outward beyond the edges of the absorbent core 44. Tab 52 can be formed by the method disclosed below prior to assembling backsheet 38 to the other components, but may also be formed after all or a portion of the components are assembled.

The components of the interlabial device 20 can be joined together in any suitable manner. The term "joined," as used herein, encompasses configurations in which an element is directly secured to another element by affixing the element directly to the other element; configurations in which the element in indirectly secured to the other element by affixing the element to intermediate member(s) which in turn are affixed to the other element; and configurations in which one element is integral with the another element, i.e., one element is essentially part of the other element.

The topsheet 42 and backsheet 38 are preferably at least partially peripherally joined using known techniques. As shown in FIGS. 1 and 2, the topsheet 42 is preferably secured to backsheet 38 along a seam 60. Seam 60 is preferably liquid impervious. The seam 60 can be formed by any means commonly used in the art for this purpose such as by gluing, crimping, or heat-sealing. The seam 60 and the area of the interlabial device 20 in the vicinity of the seam 60 should be soft, compressible, and conformable. If the seam 60 and surrounding area are too stiff or non-compressible, the wearer may experience discomfort when wearing the interlabial device 20.

In addition to the peripheral seam, the components of the absorbent interlabial device 20 can be joined together at their faces. The faces of the components of the interlabial device 20 can be joined together by adhesives, stitching, heat and/or pressure bonds, dynamic mechanical bonds, ultrasonic bonds, intermingling or entanglement of the fibers or other structural elements comprising the components of the absorbent interlabial device 20, such as by meltblowing the fibers comprising one component onto another component, extruding one component onto another, or by any other means known in the art. The components of the absorbent interlabial device 20 may be joined with water soluble adhesives in order to increase the tendency of the device 20 to disperse into a plurality of fragments in mildly agitated water (such as in a toilet). It is, therefore, desirable that the material joining the components lose strength when exposed to an excess of water, such as when placed in a toilet. Water soluble or water dispersible adhesives, such as those based on carboxymethyl cellulose, polyvinyl alcohols, starches, and the like are well known in the art.

Preferably, the interlabial absorbent device 20 of the present invention is toilet-disposable. The term "toilet-disposable", as used herein, means that the interlabial device is capable of being disposed of in a toilet. The interlabial device is preferably at least flushable. In particularly preferred embodiments, the interlabial device may also be provided with one or more of the following characteristics: dispersibility, settleability, disintegrateability, and biodegradability.

As used herein, the terms "flushable" and "flushability" refer to a product's ability to pass though typically commercially available household toilets and plumbing drainage systems without causing clogging or similar problems that can be directly associated with the physical structure of the product. It is recognized, however, that there can be many differences between the various types of toilets available. Therefore, for the purposes of the appended claims, a test to determine the flushability of a catamenial product, such as an absorbent interlabial device, is set out in the Test Methods section of this specification.

Preferably, the absorbent interlabial device 20 of the present invention is dispersible and will disperse into at least two fragments within two hours of exposure to mildly agitated room temperature water as described in the Water Dispersion Test in the Test Methods section, below. More preferably, the interlabial absorbent device 20 will be dispersed into a plurality of fragments within about 60 minutes or, even more preferably within about 30 minutes, and most preferably, within about 15 minutes as measured by the Water Dispersion Test. Preferably, the product will break into fragments which individual fragments are smaller than about 6 in$^2$, more preferably smaller than about 4 in$^2$, most preferably smaller than about 2 in$^2$. In particularly preferred embodiments of the present invention, each of the components of the interlabial absorbent device 20 will disperse into a plurality of fragments when immersed in mildly agitated water. Alternatively, the components of the absorbent interlabial device 20 may separate from each other without themselves breaking into a plurality of fragments (e.g. the topsheet 42, backsheet 38, and core 44 may break apart from each other while each otherwise remaining intact).

"Settleability" refers to the tendency of an absorbent interlabial device, such as absorbent interlabial device 20 to eventually settle to the bottom of a septic tank or other sewage treatment system rather than to float on the surface of such tanks or sewage being processed.

Disintegrateability and biodegradability can be measured in accordance with the 28 Day Sludge Test which is contained in the Test Methods section of this specification. Preferably, the absorbent interlabial device 20 comprises biodegradable materials. While biodegradable materials are preferred for the absorbent interlabial device 20, it is not necessary that each and every material used be biodegradable. For example, the device 20 may comprise superabsorbent particles which do not biodegrade, and this will not affect the ability of the overall device 20 to remain toilet-disposable and to be effectively processed in a sewage treatment system. On an overall basis, the interlabial device 20 is preferably at least about 70% biodegradable, more preferably at least about 80% biodegradable, more preferably still at least about 90% biodegradable, and most preferably, at least about 95% biodegradable.

The absorbent interlabial device 20 of the present invention in its fully assembled configuration preferably comprises at least one axis of preferred bending A. The axis of preferred bending A is preferably located generally along the longitudinal centerline L of the absorbent interlabial device 20. The axis of preferred bending A is a line or axis along which the absorbent interlabial device 20 will tend to bend or fold when subjected to compressive forces F directed inwardly in the transverse direction at the sides 32 of the device 20. The axis of preferred bending A may result naturally from the product configuration, or the device 20 may be imparted with a weakened axis or region in any or all of the topsheet 42, backsheet 38 and core 44 to create the axis of preferred bending A. Such a weakened axis may be created by any variety of known techniques such as scoring, pre-folding, slitting, or the like. The absorbent interlabial device 20 may comprise a region of preferred bending made up of a plurality of axes of preferred bending. Any number of such axes may comprise such a region of preferred bending up to an infinite number.

Figure 4:
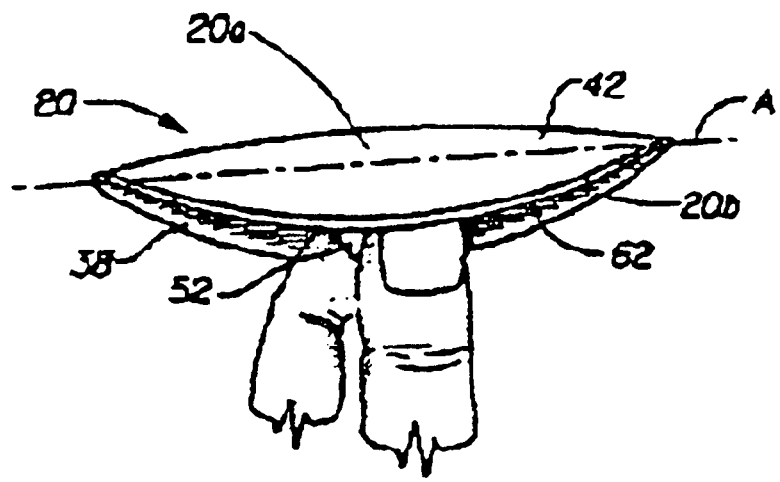
FIG. 4 shows the absorbent interlabial device shown in FIG. 1 folded along the axis of preferred bending and being grasped for insertion by the wearer's fingers.

The absorbent interlabial device 20 is folded along the axis of preferred bending A, as shown in FIG. 4, prior to insertion within the wearer's interlabial space. Once inserted, the device 20 will preferably tend to unfold slightly keeping the topsheet 42 of the device 20 in contact with the inner walls of the wearer's labia. The device 20 may be resiliently biased slightly along the axis of preferred bending A to increase the tendency of the device 20 to unfold. This allows the folded device 20 to act as a "spring" under both wet and dry conditions and, consequently, to increase the tendency of the topsheet 42 of the device to remain in contact with the inner surfaces of the labia when the absorbent interlabial device 20 is in place. A device 20 constructed according to the preferred embodiment described above, however, does not necessarily require any additional structural features to provide the ability to maintain such contact.

The absorbent interlabial device 20 described herein is preferably both flexible and compressible. Flexibility and compressibility are important to product comfort. If the absorbent interlabial device 20 is too flexible, the device is not conveniently or easily placed between the folds of the labia, if it is too stiff, the device is uncomfortable and when the user is in a sitting position, the product can be forced forward against the clitoris causing discomfort.

The absorbent interlabial device 20 of the present invention is believed to offer several advantages over previous interlabial pads. Devices constructed with the size ranges and preferred shapes described above have been found to be particularly suited for reliable insertion by a variety of wearers. Integral tab 52 provides for a suitable gripping surface for users, while not adding an additional material to the device components that must be independently disintegrateable, biodegradable, etc. The material of the tab 52 being integral with the backsheet 38, is therefore inherently as flexible as the backsheet, thereby not adding appreciable stiffness to the device.

The absorbent interlabial device 20 shown in FIGS. 1–3 (i.e. one in which the device is tapered at the ends) allows the device to easily and comfortably fit the wearer's interlabial space. A device 20 with such a tapered shape, when folded along an axis of preferred bending A (as in FIG. 4) will have a profile in which highest point along the axis of bending A (as measured in the "z"-direction) is in the vicinity of the center of the device 20 rather than at the ends. The folded configuration of the device 20 when properly sized as described above allows for consistent coverage of the walls of the labia and the vaginal introitus. Such coverage substantially reduces the incidence of "by-pass" around the device 20 by menstrual or other bodily discharges which are exhibited by previous interlabial pads.

Additionally, the absorbent interlabial device 20 described above has been found to be particularly effective at catching clots which may be formed from menstrual discharges. This clot catching attribute is believed to be enhanced by the generally increased contact of the device with the vestibule floor. In one particularly preferred embodiment, the topsheet 42 comprises a low basis weight nonwoven material such as the nonwoven rayon material described above. The absorbent core 44, as discussed above, preferably comprises a 50% rayon/50% cotton blend. Superior performance in acquiring menstrual discharges, and clots in particular, is demonstrated by the absorbent interlabial device 20 of the present invention as described above when the topsheet 42 and the absorbent core 44 comprise rayon. Without wishing to be bound by any particular theory, it is believed that such an interlabial device operates as follows. It is believed that the low basis weight topsheet provides openings for liquids to pass directly into the absorbent core, while the clots adhere better to the rayon topsheet material than many other types of topsheet materials.

The liquid impervious backsheet 38 of the absorbent interlabial device 20 is also responsible for improved product performance. As described above, the backsheet 38 reduces the likelihood of body or clothing soiling from discharges which are absorbed by the device 20.

Additionally, when the device 20 is folded along the axis of preferred bending A, the backsheet 38 will form a recess 62 which protects the wearer's fingers from soiling when the device 20 is inserted.

The absorbent interlabial device 20 may also be worn in combination with the absorbent article, such as a sanitary napkin or a pantiliner. In such a case (particularly when the interlabial device is provided with a backsheet), the absorbent interlabial device 20 will keep the sanitary napkin or pantiliner cleaner, allowing the wearer to wear the sanitary napkin or pantiliner longer than usual.

Previous interlabial pads have not provided the attributes of the device 20 of the present invention, and are thus not able to obtain the performance and comfort results described herein. Several previous pads consisted of a small generally cylindrically shaped absorbent material which is inserted into the interlabial space. These devices were not provided with a liquid impervious backsheet having an integrally-formed tab. Consequently, they are characterized by a less clean insertion and removal and may be associated with increased panty and body soiling in comparison to the present device 20.

Other previous pads did include an impervious backsheet, but the pads were much larger than the device 20 of the present invention and included significant portions which resided externally to the interlabial space. Such designs may also lead to increased body soiling as discharged bodily fluids migrate to the external surfaces of such pads. Additionally, the interlabial device 20 of the present invention is believed to offer comfort advantages (e.g. reduced wearing awareness) as compared to the above-described larger prior art pads. These and other interlabial devices were not sufficiently flexible, and did not simultaneously cover both labia when the wearer moved in certain manners (e.g. when the wearer squatted), and therefore, such devices did not conform to and spread with the labia. This resulted in less efficient collection of bodily exudates. Still other interlabial devices were folded and retained in a folded configuration. This would prevent such devices from opening and closing to conform to the labia when the wearer moved.

It has been found during development of the present invention that the absorbent interlabial device 20 better conforms to the labial vault than previously available interlabial pads. Additionally, the generally flat and folded configuration of the absorbent interlabial device 20 of the present invention is found to give a better visual indication to users as to how to insert and use the device. Therefore, the absorbent interlabial device 20 of the present invention is associated with an easier and more accurate insertion as compared to previous interlabial pads.

As previously discussed, the absorbent interlabial device 20 of the present invention is designed to be placed within the interlabial space of a wearer. As shown in FIG. 4, to use the absorbent interlabial device 20 of the present invention, the wearer grasps the tab 52 of the device 20. As shown in FIG. 4, the device 20 is then further inserted by pushing with a finger or fingers in the recess 62 formed by the folded backsheet 38. Recess 62 covers the tips of the wearer's fingers during insertion. This feature provides for a hygienic insertion of the absorbent interlabial device 20 of the present invention. The wearer may assume a squatting position during insertion to assist in spreading the labial surfaces.

FIG. 5 shows a preferred embodiment of the absorbent interlabial device 20 of the present invention inserted into the interlabial space of a wearer W. The urogenital members shown in FIG. 5 include the bladder B, the vagina V, the urethra U, the clitoris C, the large intestine I, the anus AN, the vaginal introitus VI, the hymeneal ring H, the labia minora N, and the labia majora J. FIG. 5 shows the relationship of these anatomical features of the wearer W to the absorbent interlabial device 20 when the device is properly inserted for use. Once the absorbent interlabial device 20 is inserted, the topsheet 42 tends to adhere to the inside surfaces of the labia. When the wearer is standing, the labial walls close more tightly around the folded absorbent interlabial device 20.

The interlabial device 20 is preferably at least partially retained in place by exerting a slight laterally outwardly-oriented pressure on the inner surfaces of the wearer's labia minora, labia majora, or both. Additionally, the product may also be held in place by attraction of naturally moist labial surfaces to the material comprising the topsheet 42. Optionally, the interlabial device 20, or any suitable portion thereof, such as at least one body-contacting surface of the interlabial device, can have a substance thereon to assist the interlabial device in staying in place in the desired position in the interlabial space. Preferably, the substance should adhere the interlabial device 20 to the inside surfaces of the labia minora, or alternatively to the inner surface of the labia majora, or to both the labia minora and labia majora so that it remains adhered to these surfaces (on both sides of the interlabial space) unaided by the wearer's panties, or the like, when the wearer moves in a way that the labia spread (e.g., when the wearer is squatting with her feet about shoulder width apart). This will allow the interlabial device 20 to remain in place during wearing conditions, and will also ensure that it is contacted by a stream of urine when the wearer urinates so that it will be removed on urination or be easily dislodged by a wiping action such as with toilet paper.

Typically, the unloaded interlabial device 20 will weigh less than or equal to about 5 grams. The need for a substance to assist the interlabial device in staying in place becomes more important as the loading that the interlabial device 20 is expected to hold (that is, the weight of absorbed bodily liquids) increases. This need is particularly important for the device of the present invention having additional absorbent capacity in the interior portion 54 of tab 52. The absorbent interlabial device 20 can hold any suitable amount of bodily liquids up to its absorbent capacity specified above. As the weight of absorbed bodily liquids increases, the force of gravity on the loaded interlabial device increases. This results in the need for increased ability to hold the interlabial device 20 in place, particularly when the exudate loading is greater than or equal to about 8 grams (e.g. 8, 10, 12, or 15 grams). Thus, for example, if the unloaded interlabial device 20 weighs 2 grams, and is expected to hold 10 grams of bodily exudates, the interlabial device 20 must stay in place under a force of 12 grams. Also, in some instances as the interlabial device 20 becomes loaded, if it is of a configuration which has flexible extensions, one of the flexible extensions may separate from the labia adjacent thereto while the other flexible extension remains adhered to the adjacent labia. This leads to an increased risk of soiling the wearer's undergarments and/or outer garments at heavier loadings because of the possibility that bodily exudates could travel past the side of the interlabial device that is no longer in contact with the wearer's labia. The substance used for holding the interlabial device 20 in place should have sufficient strength for holding the device securely in place, particularly against the naturally moist surfaces of the interlabial portion of the wearer's body. It should also be a material that allows the interlabial device 20 to be capable of removal without pain or trauma to the user. Preferably, the substance for holding the interlabial device 20 in place holds the device in place under the desired loadings as described above, but permits the interlabial device to be expelled from the interlabial space into the toilet when the wearer urinates. The substance, therefore, need not be adhered so that is capable of withstanding fluid pressures from the urethra of greater than or equal to about 100 centimeters of water. That is, it need only be able to withstand a pressure that is between the weight of the device when loaded up to a pressure of less than about 100 centimeters of water. (A pressure of 170 centimeters of water is the approximate maximum bear-down pressure for a typical adult human female when urinating.)

The substance for holding the interlabial device 20 in place preferably has certain additional characteristics. It should allow the interlabial device 20 to be easily placed in the proper position without discomfort, and worn without irritation. It should also preferably be biodegradable so that it is suitable for disposal in a toilet. The presence of the substance should also not interfere with the flushability of the interlabial device, if the interlabial device is of a flushable design. Preferred substances for holding the interlabial device in place are those which provide resistance to shear forces (such as those acting when the wearer walks), but can be comfortably removed using peeling forces.

The substance for holding the interlabial device 20 in place can include materials which are typically identified as adhesives, as well as materials which are not generally considered adhesives (that is, non-adhesive substances). Suitable adhesives include pressure sensitive adhesives and tacky non-pressure sensitive adhesive substances. Suitable pressure sensitive adhesives include silicone-based pressure sensitive adhesives such as polysiloxane, modified polysiloxanes, and hydrocolloid-based adhesives.

Preferably, the interlabial device is provided with a non-adhesive substance on its body-contacting surface to hold the interlabial device in place. The non-adhesive substance can be of a type that has a "tack" (that is, stickiness), or it can be of a type that does not have a "tack". Suitable non-adhesive substances include waxes (such as microcrystalline waxes, paraffinic waxes, silicone waxes, polyethylene waxes), fatty alcohols, high molecular weight alcohols, fatty acids, petroleum jelly, sealing ointments, non-ionic surfactants such as ethoxylated alcohols, ethoxylated long chain alcohols, and ethoxylated fatty acids, alkoxylated amide, alkoxylated amines, alkyl amido alkyl amines, alkyl substituted amino acids, moisture-activated substances, and combinations thereof. Another suitable non-adhesive substance is the fat substitute OLEAN manufactured by the Procter & Gamble Company of Cincinnati, Ohio under U.S. Pat. No. 5,085,884 issued Feb. 4, 1992 and U.S. Pat. No. 5,422,131 issued Jun. 6, 1995, both to Young, et al. and U.S. Pat. No. 5,422,131 issued to Elsen, et al. Without wishing to be bound by any particular theory, it is believed that such materials may hold an object in place due to high viscosity or surface tension.

Moisture-activated substances are substances which have little or no initial tack (that is, they will be dry to the touch), but when contacted by moisture (preferably relatively small amounts of moisture), they become viscous and develop a tack. Preferred moisture-activated materials for use in the present invention lose most of their tack when flooded with an excess of moisture such as when the wearer urinates. Moisture-activated substances are particularly preferred for use with the interlabial device 20 because they can make the interlabial device easier to apply than pressure sensitive or tacky adhesive-coated devices because the product does not adhere to the body as it is inserted and because it is not necessary for the wearer to spread her labia and risk soiling her hands when placing the interlabial device as may be necessary when adhesives are used. In addition, moisture-activated substances will not tend to stick to the wrong portions of the wearer's body when the product is placed between the labia and become mis-oriented, as will adhesives. They are also particularly useful for holding the interlabial device securely against this portion of the wearer's body since moisture is naturally present. In other words, they are capable of hydrating in vivo.

Some particularly preferred moisture-activated substances are polyethylene glycols ("PEGs"), sodium carboxymethylcellulose (preferably USP (U.S. Pharmacopia) grade), alcohols, glycols (dihydric alcohols) such as propylene glycols, hexylene glycols, polyols which contain three or more hydroxyl groups, such as glycerin, and sugar alcohols and other molecules capable of hydrogen bonding by contact with the water in the interlabial region, starches, surfactants such as polyoxyl alkylates (polyoxyethylene sterates), ethoxylated alcohols, sugar surfactants, and sugars (such as glucose, fructose, and sucrose), or combinations or mixtures thereof. The foregoing substances may be used alone, in combination with each other, such as in combination with polyethylene glycols, or in combination with pectin, guar gum, locust bean gum, hydroxypropyl guar gum, polyglucomanum gum, cationic guar gum, anionic guar gum, alginate, xanthan gum, or combinations or mixtures thereof, and combinations or mixtures thereof with polyhydric alcohols.

Polyethylene glycols ($HO—(CH_2CH_2—O)_n—H$), also abbreviated as PEG's, are substances like those found in cough syrups to coat a person's throat. Polyethylene glycols are available from Union Carbide under the trademark CARBOXWAX. PEG 200 to PEG 600 (PEGs with molecular weights between 200 and 600) are liquid at or below 80° F. (27° C.). PEG 900 to PEG 20,000 and above are solid at or below 80° F. (27° C.). All are at least 60% soluble in water at 20° C. Preferably, the higher molecular weight PEG's which are in solid form are used. However, the lower molecular weight PEG's can also be used. Polyethylene glycols can be applied to the body-contacting surface of the interlabial device using any conventional processing steps, which are described in greater detail below. Once applied, they will typically dry to a non-tacky powder form. Polyethylene glycols, since they are water soluble, are also capable of losing their tendency to stick to the labia when the wearer urinates, so the interlabial device will be expelled by urination as intended. Their water solubility also ensures that they will not interfere with the ability of flushable interlabial devices to flush down a toilet, and will not float in the toilet as will some other products. (The tendency for other products to float reduces the ability of the products to go down the toilet when flushed and results in an extremely inconvenient situation for users who have to remove such products from the toilet bowl, and then dispose of these products.) Polyethylene glycols are also biodegradable, unlike most pressure sensitive adhesives, which are silicon-based.

One particularly preferred moisture-activated substance comprises a mixture of 1.75 g sodium carboxymethylcellulose, USP; 0.25 g polyethylene oxide, NF; and 125 ml distilled water. The mixture is preferably applied in a total amount of 0.15 g per each interlabial device (wet weight) if the mixture is only applied to the sides of the product, or in a total amount of 0.30 g per interlabial device if the mixture is to be applied to the entire body-contacting surface of the product.

The substance for holding the interlabial device 20 in place can be combined with other substances before it is applied to the interlabial device. Such other substances can serve as a component of the substance for holding the interlabial device in place, or as a carrier for the substance for holding the interlabial device in place. Non-limiting examples of substances that can serve in either of these manners are lotions, emollients, and mineral oil. For example, the substance for holding the interlabial device in place can be a polyethylene glycol that is mixed in a lotion formula that provides lubricity during the insertion process and develops tack when contacted by moisture. In another example, an emollient can be used as a carrier for PEG's which are in particulate form. In still another example, the PEG's can be in liquid form, and can serve as a carrier for other materials. Such other materials may include, but are not limited to, spermicides.

The substances described above can be applied to the body-contacting surface of the interlabial product in an intermittent pattern, a continuous pattern, or in a pattern that has both continuous and intermittent portions. Applying the substances in an intermittent pattern may be useful if it is desired to minimize interference of the substances with acquisition of liquids into the interlabial device 20 since liquids can be transported into the absorbent core between the intermittent zones of the substance. Applying the substances in a continuous pattern may be useful if it is desired to use the contact that the substance makes to the wearer's body to create a barrier to the flow of exudates over the body-contacting surface of the interlabial device. However, the application of the substances in a continuous pattern need not form an impermeable barrier which prevents menses or urine from being absorbed by the interlabial device 20.

The substance can be applied in any suitable manner, such as by spraying, padding, use of transfer rolls, or by printing, such as by gravure or screen printing. The substance can be applied directly to the interlabial device, or it may be applied to another material or component which is then adhered to the desired portion of the interlabial device.

The substance can be placed on any suitable portion of the interlabial device 20. The substance can be placed on the entire body-contacting surface of the interlabial device 20, or on a portion thereof. For example, the substance can be placed on all or a portion of the body-contacting surface of the main body portion 22. If the interlabial device is of a type that comprises a central absorbent portion and flexible extensions extending therefrom, the substance can be placed on the central absorbent portion, the flexible extensions, or both the central absorbent portion and the flexible extensions. The substance can, thus, be placed on a central region of the interlabial device 20, but not on the peripheral portions of the interlabial device. More preferably, however, the substance may be placed on the peripheral portions of the body-contacting surface of the interlabial device, but not in the central region. Locating the substance in the latter manner may be advantageous if it is desired to minimize any tendency for the substance to interfere with acquisition of bodily liquids into the interlabial device 20. The substance can also be used to create a seal to prevent the flow of exudates toward the ends (and/or sides) of the device. The substance can cover any of the following percentages of the surface area of the body-contacting surface of the main body portion 22, the central absorbent portion, the flexible extensions, or the entire body-contacting surface of the interlabial device (greater than or equal to about): 5%, 10%, 20%, 30%, 40%, 50%, 60%, 70%, 80%, 90%, or 100%.

The substance can be applied to the interlabial device 20 in any suitable and sufficient quantity. For these purposes, the quantity of the substance applied to the interlabial device 20 will be expressed in terms of the total product weight including the device and the weight of the substance. Preferably, the substance constitutes less than or equal to about 20%, more preferably less than or equal to about 10%, and most preferably less than or equal to about 5% of the total product weight, so as not to excessively contribute to the overall weight of the interlabial device. This permits more of the total product weight to be dedicated to providing absorbent capacity.

There are many possible specific embodiments of interlabial devices with various substances thereon for assisting the interlabial device in staying in place in the desired position in the interlabial space. The interlabial device can have one or more of the substances described herein applied thereto in any of the patterns of application described herein.

For example, the main body portion 22 of an interlabial device having the configuration shown in FIGS. 1–3, may be provided with a biocompatible adhesive to assist the adhesion of that portion of the interlabial device to the inside surfaces of the wearer's labia. The strength of such an adhesive should be selected to assist the absorbent interlabial device 20 in staying in place, while still allowing for reliable, and comfortable removal of the device from the wearer's interlabial space. Examples of suitable adhesives include hydrocolloids or hydrogel adhesives that are currently available in the market, and acrylic-based adhesives.

In other embodiments, any desirable combinations of the substances described herein, or combinations of patterns of application, or both may be used. One non-limiting example would be to apply a combination of an adhesive and a non-adhesive substance to the interlabial device. For example, in the case of an interlabial device having the configuration described in U.S. Pat. No. 5,762,644, issued to Osborn, et al., a polyethylene glycol can be provided on the body-contacting surface of the central absorbent portion, and a pressure sensitive adhesive can be provided on the flexible extensions. Preferably, if adhesives are used, they are applied to portions of the interlabial device that do not block or retard the flow of urine from the urethra into the absorbent interlabial device 20.

In another example, the interlabial device 20 may be provided with one of the substances described herein (such as an adhesive) around the periphery of the body-contacting surface of the interlabial device to assist the device in staying in place adjacent to the wearer's labia. The substance can be applied in a continuous or an intermittent pattern, or a pattern which is partially continuous and partially intermittent. A swelling absorbent material can be placed inside the area defined by the substance. If a complete seal with the wearer's body is desired, this swelling absorbent can be used to eliminate any gaps or void spaces that may occur adjacent to the wearer's body that may occur due to misplacement of the interlabial device relative to the wearer's labia, and create a self-sealing device. Some non-limiting examples of swelling absorbent materials include, but are not limited to superabsorbent, hydrogel forming materials, absorbent foam materials, modified cross-linked cellulosic fibers, and compressed absorbent materials, such as those used in tampons.

Numerous other embodiments and properties for the substance for holding the interlabial device in place are also possible. For example, the substances described herein preferably have moisture vapor transmission rates sufficient to maintain the natural state of hydration of the labial tissue. Suitable moisture vapor transmission rates are not less than about 300 gm m/hr at a relative humidity difference of 10 to 100%. In addition, any of the substances described herein can be used in conjunction with, or be combined with emollients such as those described in U.S. Pat. No. 5,609,587 entitled "Diaper Having a Lotioned Topsheet Comprising a Liquid Polyol Polyester Emollient and an Immobilizing Agent", issued Mar. 11, 1997 to Roe, and U.S. Pat. No. 5,643,588 entitled "Diaper having a Lotioned Topsheet" issued on Jul. 1, 1997 to Roe, et al.

In addition to the various embodiments of the substances for holding the interlabial device 20 in place which are described herein, the interlabial device can be provided with other optional features. For example, it has been found that the interlabial device of the present invention provides a substantial noticeable benefit to the user in controlling odors associated with body exudates. Additional odor controlling agents may be added to seek further reductions in odors. Such odor controlling agents include, but are not limited to activated charcoals, zeolites, silica, polyacrylic acids (superabsorbents), certain quaternary compounds, triethyl citrate, cyclodextrin, or any combinations thereof. Particularly preferred cyclodextrin compounds are described in U.S. Pat. No. 5,429,628 issued to Trihn, et al. and U.S. Pat. No. 5,780,020 issued to Peterson, et al. In addition, deodorants can be added to further mask these odors.

Further, over-the-counter vaginal drug actives can be added for one or more of the following purposes: cleansing, providing soothing and refreshing effects, deodorizing, relieving minor irritation, reducing the number of pathogenic microorganisms, altering pH so as to encourage the growth of normal vaginal flora, producing an astringent effect, lowering surface tension, producing a mucolytic effect, or producing a proteolytic effect. Such over-the-counter vaginal drug actives include: calcium propionate, dioctyl sodium sulfosuccinate, nonoxynol 9, octoxynol 9, potassium sorbate, povidone-Iodine (PVP-Iodine), sodium lauryl sulfate, and sodium propionate.

In these or other embodiments, the interlabial device 20, or any of the components thereof, can be made of extensible and/or stretchable materials to aid in the ability of the interlabial device to remain in place when forces are exerted on the interlabial device during wear. It is believed that such materials are particularly useful for any wrapping or topsheet on the interlabial device and on for any flexible extensions, or for both of these types of components. It is also within the scope of this specification for such extensible and/or stretchable materials to be used as components of the absorbent articles described herein with or without any of the substances described herein for assisting these absorbent articles for staying in place against the wearer's body. That is, this specification also describes a novel interlabial device made from at least some components that are extensible and/or stretchable.

However, it is particularly desirable to form the interlabial device or some portion thereof from extensible and/or stretchable materials when substances are applied to the interlabial device to assist the interlabial device in staying in place in the interlabial space. For example, if the interlabial device has portions that are adhered to the labia, some extensibility is preferably present for improved comfort and to reduce the possibility of irritation. Specifically, it is desirable not to restrict the movement of the wearer's labia when the wearer's body moves. Suitable extensible materials that could be used for the components of the interlabial device are described in U.S. Pat. No. 5,611,790 entitled "Stretchable Absorbent Articles", which issued to Osborn, et al. on Mar. 18, 1997.

Figure 6:
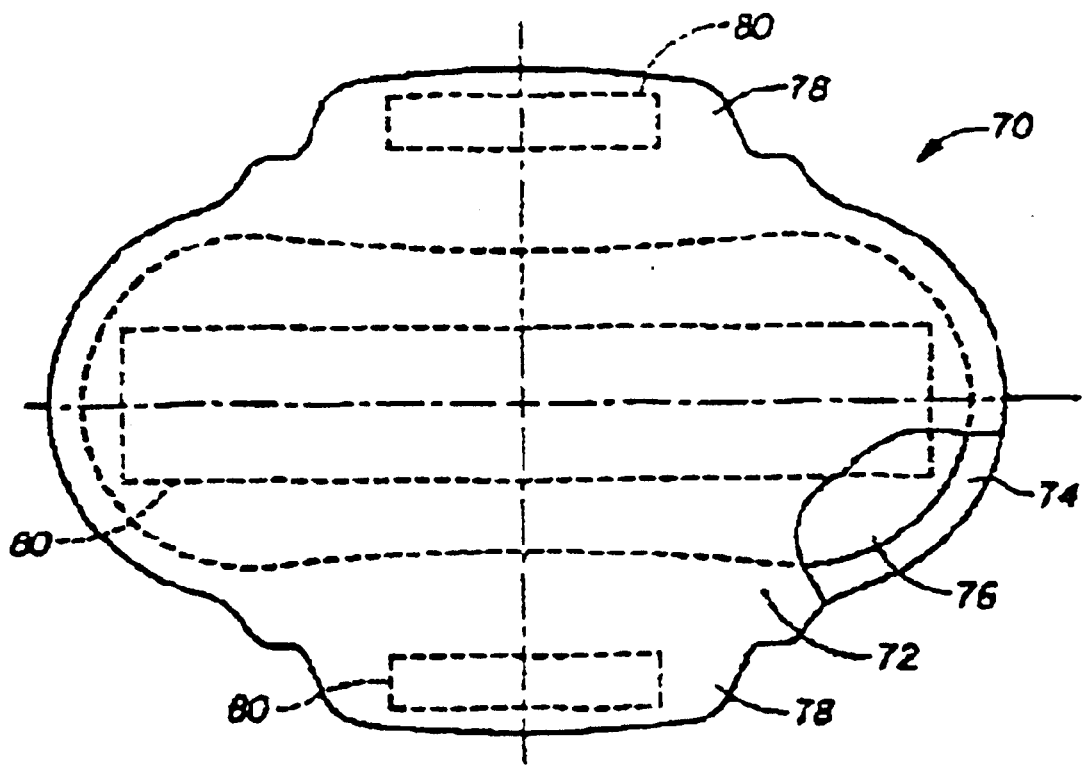
FIG. 6 is a prior art sanitary napkin which may be used in a method of using a system of feminine hygiene products or as part of a feminine protection kit with the absorbent interlabial device of the present invention.

The absorbent interlabial device 20 can be worn as a "stand alone" product. Additionally, superior performance in reducing body and clothing soiling over extended periods of wear time (such as overnight) can be obtained by using the absorbent interlabial device 20 as part of a "system" of feminine hygiene products. One such system which is effective in reducing soiling is an absorbent interlabial device, such as absorbent interlabial device 20, which is worn simultaneously with a sanitary napkin, such as sanitary napkin 70 (shown in FIG. 6).

Such a system of an interlabial device in combination with a sanitary napkin is more effective than either a sanitary napkin or an interlabial pad worn alone. The absorbent interlabial device used in the system of the present invention may, and preferably does, have all of the preferred attributes of the absorbent interlabial device 20 described above, and can include the formed tab 52. The sanitary napkin 70 of the present system may be any suitable conventional sanitary napkin. The sanitary napkin 70 preferably comprises at least a liquid pervious topsheet 72, a liquid impervious backsheet 74 joined to said topsheet, and an absorbent core 76 positioned between the topsheet 72 and the backsheet 74. Additionally, the sanitary napkin 70 preferably includes a pressure sensitive adhesive 80 disposed on the garment facing side of the backsheet 74. The adhesive 80 allows the sanitary napkin 70 to be adhered to the crotch portion of the wearer's undergarments. When the undergarments are worn in their usual wearing position, the sanitary napkin 70 will rest adjacent the pudendal region of the wearer's body. The sanitary napkin 70 may also be provided with additional features commonly found in sanitary napkins, including "wings" or "flaps" such as wings 78. A suitable sanitary napkin for use in the above-described system is the "ALWAYS" Ultra thin Maxi with Wings sanitary napkin which is manufactured and packaged by the Procter & Gamble Company of Cincinnati, Ohio under one or more of U.S. Pat. No. : B1 4,589,876; 4,687,478; 4,950,264; 5,009,653; 5,267,992; 5,354,400; 5,389,094; 5,489,283; 5,620,430; 5,704,930 and Re. 32,649. Other sanitary napkins are also acceptable, such as those without wings 78 and those which are not of the "Ultra-thin" type.

In order to use an absorbent interlabial device and a sanitary napkin as a system of feminine hygiene products, the wearer inserts the absorbent interlabial device into her interlabial space and places a sanitary napkin in the crotch portion of a panty-type undergarment. These two steps may be performed in either order. Some women will prefer to place the sanitary napkin in the panty crotch first in order to catch and absorb drops of menstrual flow which might be released prior to the time that the absorbent interlabial device can be inserted. Other women will choose to first insert the absorbent interlabial device. After the absorbent interlabial device is inserted and the sanitary napkin is positioned in the undergarment crotch, the undergarment is pulled up into its usual wearing position. Consequently, the sanitary napkin will rest adjacent the pudendal region of the wearer's body and will be worn simultaneously with the absorbent interlabial device.

Preferably, the absorbent interlabial device used with the above-described system is changed each time the wearer urinates. The associated sanitary napkin may be worn for longer periods of time (i.e. beyond the changing of the absorbent interlabial device) because the bulk of the bodily fluids will be deposited on and absorbed by the interlabial device as opposed to the sanitary napkin. Particularly if the absorbent interlabial device 20 is provided with a tab 52 for removal, some women will prefer to remove the absorbent interlabial device 20 prior to urination, then subsequently re-insert the same device 20 if it has not yet absorbed near its full capacity. In addition, if a woman chooses not to dispose of the interlabial device by flushing it down the toilet, the tab 52 provides a hygienic way for the woman to remove the product and dispose of it.

The sanitary napkin and the absorbent interlabial device of the above-described system may be packaged in a common package as a feminine hygiene "kit." Such a kit facilitates use of the system of the present invention. Preferably, the packaging associated with such a kit will include instructions on how to use the absorbent interlabial device and the sanitary napkin according to the above-described method as a system of feminine hygiene products.

Figure 7:
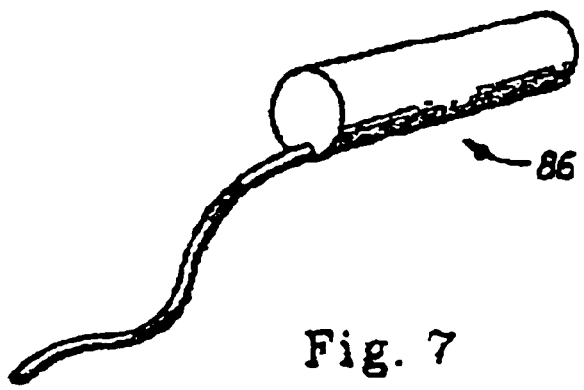
FIG. 7 is a typical prior art tampon which may be used in a method of using a system of feminine hygiene products or as part of an additional feminine protection kit with the absorbent interlabial device of the present invention.

An alternate suitable system of feminine hygiene products comprises the absorbent interlabial device 20 of the present invention used simultaneously with an absorbent tampon, such as tampon 86 shown in FIG. 7. The absorbent tampon of this system of feminine hygiene products may be any suitable conventional catamenial tampon including any of the tampons sold under the trademark "TAMPAX" and distributed by The Procter & Gamble Company of Cincinnati, Ohio. The tampon used may be either of the applicator insertion or digital insertion type and any suitable applicator known in the art may be used. The tampon is first inserted into the vaginal cavity of the wearer. Following insertion of the tampon, the absorbent interlabial device is inserted into the interlabial space of the wearer. The interlabial device and the tampon are then worn simultaneously for a period of time. The absorbent interlabial device may be removed and changed each time the wearer urinates, or may be removed then reinserted subsequent to urination.

Similarly, the absorbent tampon and the absorbent interlabial device 20 of this system may also be packaged in a common package as a feminine hygiene kit. This kit facilitates use of the alternate system of the present invention.

Systems and associated kits of the present invention may also comprise the simultaneous use of an absorbent interlabial device, tampon, and sanitary napkin. Kits comprising all three types of feminine hygiene products may also be packaged in a common package and include appropriate instructions for use of such systems.

In addition to the systems described above, the absorbent interlabial device 20 may be worn simultaneously with a pantiliner, or incontinence pad for menstrual or incontinence use. The absorbent interlabial device 20 described above may be combined and packaged with a pantiliner, an incontinence pad, or a sanitary napkin to form a feminine urinary incontinence kit. Such an incontinence kit preferably includes appropriate packaging material instructing the wearer as to how to use the feminine hygiene products for light incontinence protection. The interlabial device 20 can be worn in conventional panties, or it can be used with menstrual shorts.

Numerous alternative embodiments of the absorbent interlabial device of the present invention are possible. For example, these products are designed to be removed by urination, although an alternative extraction string or loop may be used. These products may also be used with emollients and/or medicinal treatments. For example, a suitable emollient composition for use on the absorbent interlabial device 20 of the present invention is comprised of about 50% petrolatum (such as White Protopet 1S made by Witco Corp.), about 35% Cetearyl Alcohol (a mixed linear $C_{16}$–$C_{18}$ primary alcohol made by The Procter & Gamble Company under the name TA-1618), and about 15% Ceteareth-10 made by BASF. An emollient coating of about 0.03 g/pad has been found to be suitable.

The absorbent interlabial device 20 of the present invention may be provided with a visual indication on the center of the topsheet 42 designating the area of greatest absorbent capacity of the device 20. Such an indication may consist of a differently colored region such as a pink oval. The indication may be about 12 mm wide and about 20 mm long. The absorbent interlabial device 20 may also be provided with a visual change indication. In other words, the device 20 may have a ring, bonding pattern, compression lines, or other visual indicator provided on the surface of the topsheet 42 at a predetermined distance inboard from the seam 60. When absorbed bodily discharges reach the visual change indication or outboard of the change indication, the user knows to replace the absorbent interlabial device 20. Such a change indication is particularly useful to users who remove the device 20 prior to urination and then re-insert the same device 20 if it has not yet reached its absorbent capacity.

Figure 8:
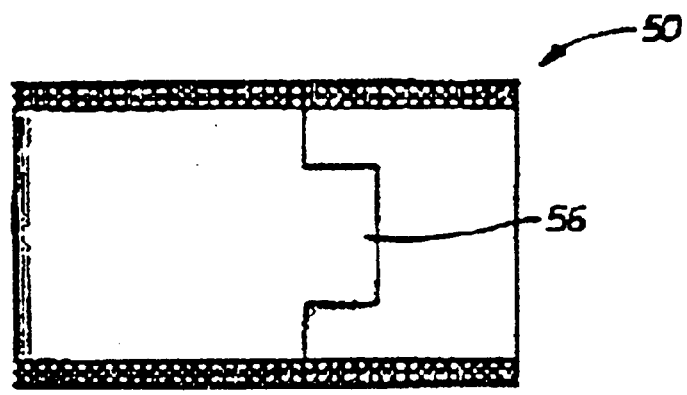
FIG. 8 is front view of an individual package for the interlabial device in an unopened condition.
Figure 9:
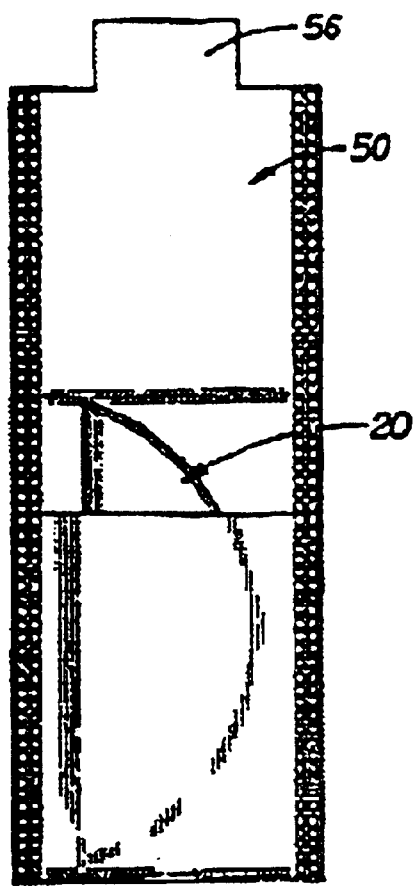
FIG. 9 is front view of the individual package in an opened condition with the folded interlabial device inside.

If desired, the absorbent interlabial device 20 may be packaged in an individual package, such as the package 50 shown in FIGS. 8 and 9. The individual package 50 may be comprised of a number of suitable materials, including films and toilet-disposable materials. In FIGS. 8 and 9, the package 50 is made of a film which is frangibly sealed at the edges. The package 50 is provided with an opening tab 56 which can be of any suitable configuration. Suitable methods for frangibly sealing packages are described in U.S. Pat. No. 4,556,146 issued to Swanson and U.S. Pat. No. 5,462,166 issued to Minton, et al. Suitable tabs for such a package are described in U.S. Pat. No. 5,413,568 issued to Roach, et al.

APPARATUS AND METHOD OF MAKING

As disclosed above, the components of device 20 can be assembled in any suitable manner. The device 20 can be assembled by hand, for example, by cutting, forming, and arranging the components as disclosed and performing any necessary joining and tab (protrusion) forming operations. However, the device is preferably assembled in commercial quantities with the aid of automated or semi-automated equipment known in the art. For example, the backsheet, topsheet and absorbent core can be supplied from roll stock, layered, joined by adhesive, and die cut to size using methods and equipment known in the art. However, to make the absorbent device 20 of the present invention having an integral tab 52 requires an additional apparatus for, and the additional step of, forming an integral protrusion in the backsheet, which apparatus and method is disclosed in detail below.

Tab 52 may be formed as a protrusion of the backsheet by blow-molding a suitable polymer into a suitably-shaped mold. Tab 52 may be formed by reforming the backsheet material using heat and pressure to form the backsheet to a mold surface, such as a hot "knife" pressed into the backsheet. But tab 52 is preferably formed by strain-induced plastic deformation of the backsheet 38 material prior to assembling any of the other components of device 20, or it may be deformed after assembling some or all the components in their layered configuration.

Figures 12, 13:
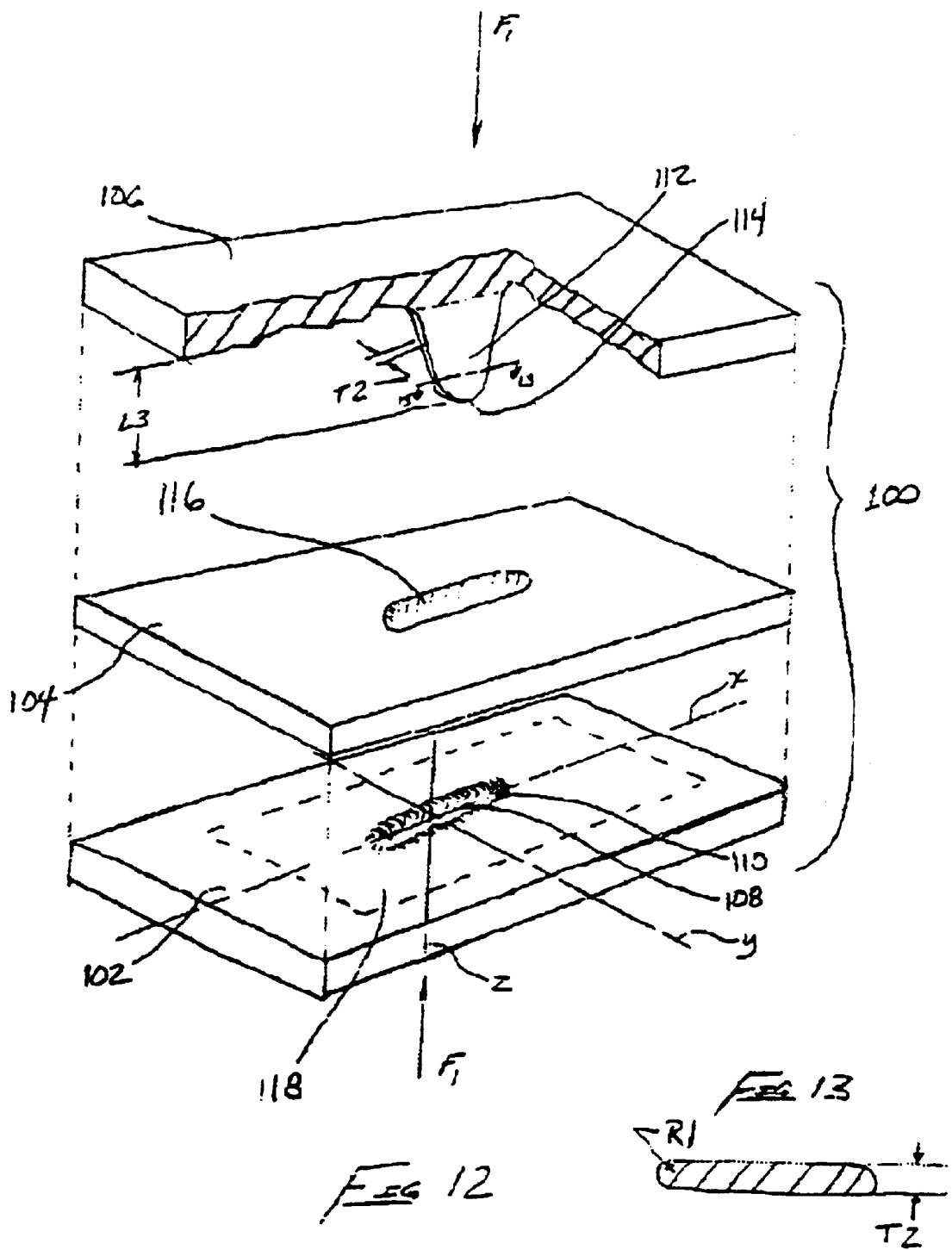
FIG. 12 is an schematic perspective representation in partial cross section of an apparatus for forming the integral tab on an interlabial device of the present invention.
FIG. 13 is a cross-section of the forming member of FIG. 12 taken along line 13—13 thereof.

FIG. 12 shows one apparatus 100 for forming a tab 52 on the device 20 of the present invention. Apparatus 100 is suitable for small batch production of the device of the present invention and comprises: a female forming member 102, shown in FIG. 12 as a flat plate having a void area, such as elongated slot opening 108; a compression member 104, shown in FIG. 12 as a flat plate having an elongated slot 116; and a male forming member, such as male forming member 106, shown in FIG. 12 as a flat plate having forming protrusion 112 integrally or separately joined thereto. Each component plate of the apparatus 100 has an x-axis, a y-axis, and a z-axis, the axes corresponding directionally to the axes of the interlabial device 20 as disclosed above.

Female forming member 102 comprises an opening 108 which preferably is slotted, having radiused edges 110. That is, the edge of opening 108 is preferably not sharp enough to cause rupture or tearing of the backsheet material during formation of the tab as disclosed herein. Thus, in a preferred embodiment, the edge has a radius of curvature of at least about 3 mm (about ⅛ in.), and more preferably about 6 mm (about ¼ in.). The radius of curvature can be as great as 12 mm (about ½ in.). As the radius of curvature becomes greater, more material is provided for strain inducement, i.e., less material is constrained by compression member 104 in the region of strain inducement.

Male forming member 106, and compression member 104 have a forming protrusion 112, and an opening 116, respectively. Forming protrusion 112 is in operative alignment with opening 116 and comprises generally rounded contours, the rounded contours and overall shape corresponding to the preferred finished shape of tab 52, as shown in FIG. 3. The forming protrusion 112 can be generally flattened, having a thickness T2 with a radiused edge sufficient to form tab 52 without cutting or otherwise causing the material to tear. For example, as shown in FIG. 13, a forming protrusion having a width T2 of about 2 mm (about ¹⁄₁₀ in.), and a radius of curvature R1 on the edge of about T2/2 can successfully form a tab 52 in polyethylene having a thickness of about 0.012 mm (about 0.0005 in).

The forming protrusion should be of sufficient length L3 to extend through the thickness of the compression member 104, and form a tab having sufficient length L2, as shown in FIG. 2. In practice, L3 should be a predetermined distance greater than the sum of the thickness of compression member 104 and the desired finished length L2 to permit some recovery of the strained material to occur, yet maintain the desired length L2 after the straining force is removed. The predetermined distance greater of L3 is dependent upon the particular backsheet material and desired length of tab 52. In one embodiment it was found that to have a tab 52 having a finished length of 15 mm, the backsheet material was strained to a corresponding length of 18 mm.

The female forming member 102, compression member 104, and male forming member 106 each cooperate in an aligned manner in the x and y axes, thus allowing cooperative engagement, preferably linear engagement, in the z-axis as discussed herein. In operation, the backsheet material 38, or the backsheet material with the absorbent core positioned in place thereon, is placed flat in the region 118 indicated by dashed lines in FIG. 12. The backsheet and/or absorbent core material may be any desired shape at this time, and may be die cut to the preferred generally oval shape in a subsequent step. However, regardless of the shape of the backsheet at this time, to produce a tab 52 aligned centrally with the finished device, the backsheet material should be aligned such that the resulting x-axis of the device 20 is in alignment with the x-axis of the apparatus 100. Likewise, the y-axis should be so aligned.

Once the backsheet and, if desired, the absorbent core, are in position on female forming member 102, compression member 104 is brought into face to face compression contact with the female forming member 102 to "sandwich" the backsheet under a predetermined pressure between the two plates. The amount of pressure can be adjusted as needed to prevent undesired movement of the backsheet in the compressed region during the forming operation described below. If necessary, the opposing faces of the female forming member 102 and compression member 104 can be treated with a relatively high coefficient of friction substance or material to aid in preventing the backsheet/absorbent core from moving during the tab formation process. For example, a thin sheet of soft rubber can be applied to either or both opposing faces to effect a higher frictional stabilization of the backsheet/absorbent core in the compressed region. Thus, ideally, tab formation is due only to plastic deformation of the backsheet material in uncompressed regions, and not due to the backsheet material simply being pulled down through opening 108.

Plastic deformation is believed to produce a more desirable tab due to the increase in overall material surface area without an increase in actual material used. Thus, no additional weight is added to the finished device, which, as discussed above, contributes to the reliability of the device in staying in place under loaded conditions.

It is contemplated that in practice, some of the tab formation may be due to some shifting of material, or pulling down into opening 108, which is permissible, and may even be desirable for some tab configurations or material selections. However, the currently preferred tab formation method and apparatus minimizes such shifting of material within the compression region.

Without being bound by theory, it is believed that the strain induced drawing, i.e., plastic deformation, characteristics of the material is dependent in part upon the geometry of the apparatus. For example, the material that results in tab 52 is drawn from the material immediately overlying opening 108 as well as the material overlying the radiused edge 110. In other words, the material overlying opening 108 and 110 is not in compression, and can therefore be strained to form tab 52. Thus, for a larger radius on radiused edge 110, more material is available to be strained, or drawn, to form tab 52. Therefore, for materials having relatively lower strain limits, a larger radius may permit the desired tab length.

Once the compression member 104 is in operative position (i.e., in pressurized face to face contact) with female forming member 102, male forming member 106 is moved linearly in the z-direction in operative alignment such that forming protrusion 112 extends through opening 116 in compression member 104 and contacts the backsheet material/absorbent core adjacent the opening 108 in female forming member 102. Male forming member 106 continues in the z-direction a sufficient amount to form tab 52 by plastic deformation. The maximum amount of strain, and the maximum rate of strain, are determined primarily by the material properties of the backsheet material, and can be determined accordingly.

In general, to produce a tab 52 having sufficient length L2 for a given material, the material should be able to withstand a strain of at least about 50% before rupture, more preferably at least about 100%, and most preferably at least about 200%. While strain rate is not critical to the formation of the present invention, strain rate characteristics are important when considering commercial, high-speed production of tabs. Therefore, for relatively high-speed production, as permitted by the apparatus described below, it is desirable that the backsheet material be able to withstand strain rates of at least about 10 mm/sec, more preferably at least about 20 mm/sec, and most preferably at least about 30 mm/sec.

The basic apparatus method of forming the tab with the apparatus shown in FIG. 12 can take various forms without departing from the scope of the present invention. For example, as discussed above, it may be desirable to provide the absorbent core material in position on the backsheet material prior to forming the tab. Thus, the backsheet material can be disposed in position on female forming member 102, and the absorbent core material disposed in position on the backsheet material. As male forming member 106 is operatively actuated, forming protrusion 112 first either pierces or otherwise deforms the absorbent core material and then deforms the backsheet material. Depending on the absorbent core material and the geometry of the forming member 112, some of the absorbent core may be drawn into the interior portion 54 of tab 52 during the tab formation process. This may be considered desirable as it provides an alternative fluid storage capacity that is disposed a greater distance from the wearer's body.

Additionally, the basic apparatus and method disclosed with reference to FIG. 12 can be modified in its operation by forming a hinged arrangement that does not rely on linear engagement of the forming member, for example. By having at least the forming member 106 hingedly rotatable about one of its edges, strain induced deformation can be effected by rotating the hinged members into a closed, face to face relationship while the backsheet and/or absorbent core are held in compression as disclosed above.

In another variant on the basic process described with respect to FIG. 12, other components can be superimposed over the backsheet material and/or absorbent core in the region coincident the opening 108 in female forming member 102, but not in the compressed region prior to tab formation. For example, a packet, e.g., particulate material in a gauze wrap, of absorbent gelling material can be disposed such that when forming protrusion 112 is operatively actuated, it first contacts the packet of absorbent gelling material, ultimately pushing it down and into the interior portion 54 of tab 52. Thus, the absorbent gelling material provides even greater fluid storage capacity in the tab, away from the wearer's body. Absorbent gelling material can be provided on a carrier, such as a gauze wrap that resists puncture or tearing during tab formation. Absorbent gelling powder can also be provided on an adhesive tape that is disposed as described herein, and drawn into the interior portion of the tab. Similarly, absorbent gelling material may be provided in liquid form, e.g., a liquid dispersion, or powder or granules as discrete particles in the absorbent material itself.

The process described with respect to the apparatus 100 shown in FIG. 12 can be adapted to a continuous, relatively high-speed, process for forming interlabial devices from continuous web material, i.e., roll stock. For example the tab forming apparatus 120 shown in FIG. 14 can be positioned in line with existing equipment designed to form absorbent devices such as sanitary napkins from roll stock. In general, each component, i.e., the backsheet, topsheet, and absorbent core can be provided as webs and supplied as roll stock. The webs are fed or guided into appropriate equipment to layer, bond, die cut, and otherwise form the webs into a disposable absorbent article. In the method of the present invention, the apparatus shown in FIG. 14 can be placed in line, preferably prior to bringing the topsheet into a layered relationship with a backsheet and core, as discussed below.

Figure 14:
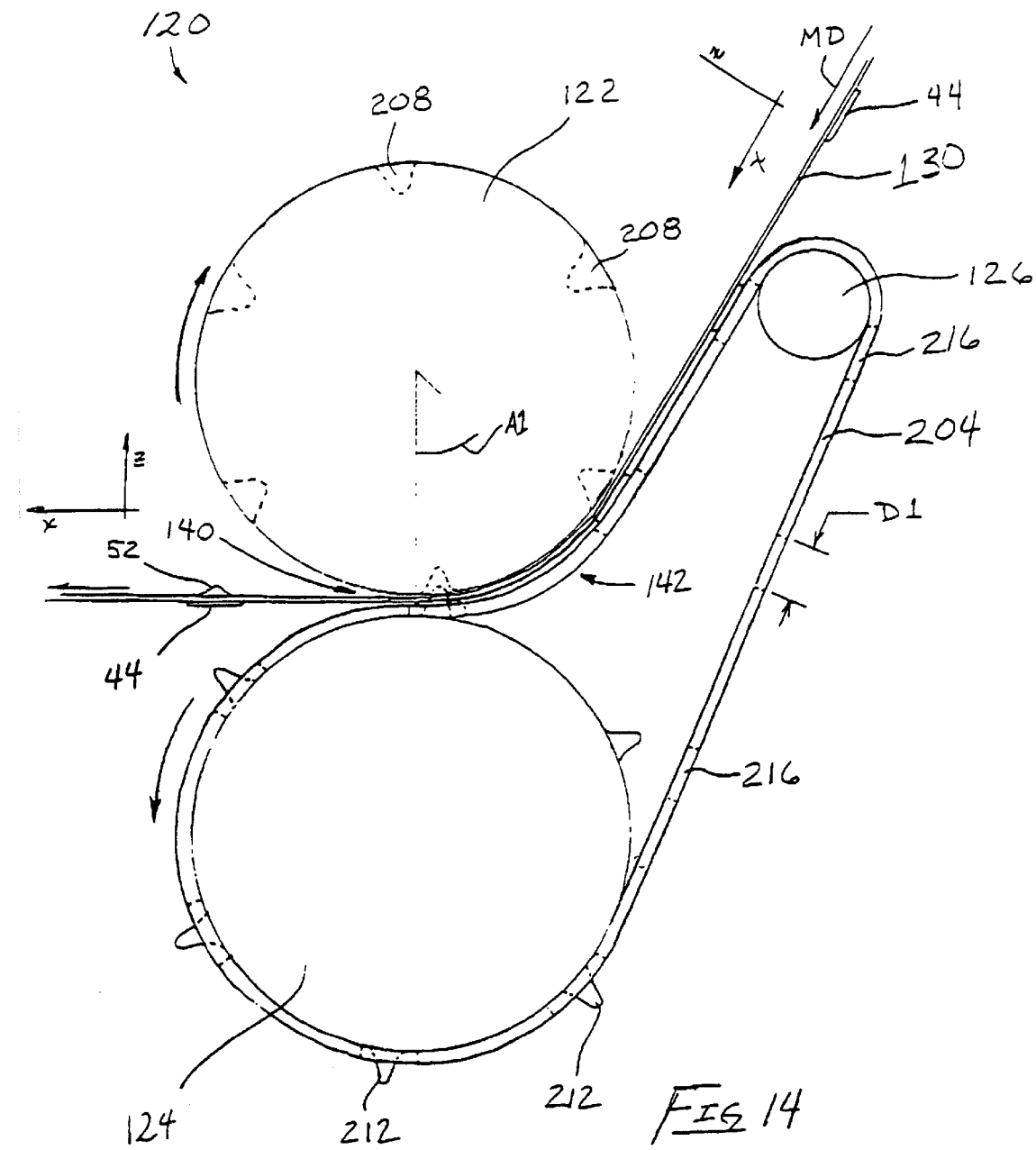
FIG. 14 is a schematic representation of an apparatus for continuous formation of the integral tab on an interlabial device of the present invention.

As shown in FIG. 14, a tab protrusion can be formed by the method of the present invention by the continuous process apparatus 120. Web backsheet material 130 can be provided in continuous strip, or web, form from roll stock, such as a wound roll of polyethylene, for example. Backsheet material 130 can have tab protrusions formed prior to being joined, laminated, or otherwise assembled with other components such as absorbent core material or topsheet material, if used. However, in a preferred embodiment, the absorbent core material is die cut to size and shape, and positioned in spaced relationship on backsheet material prior to tab formation. Therefore, as shown in FIG. 14, absorbent core material 44 can be die cut to its finished dimensions and disposed on, and adhered to if necessary, web material 130 in registered, spaced relationship, prior to entering apparatus 120.

Absorbent core material 44 can be provided as a pad, batt, or other generally planar web prior to being die cut by known methods. For example, a web of nonwoven absorbent material can be guided into the nip of a rotary die cutter (not shown) having appropriately shaped die cutting means. As the die cut absorbent material exits the nip of the die cutting means, it can be urged onto the backsheet web material 130 in spaced relationship by known methods. For example, the absorbent core material 44 can be deposited by gravity, or can be urged in position by the use of positive pressures, for example air pressure. In another embodiment, the absorbent core material 44 can be adhesively joined to the backsheet web material in the spaced relationship, as shown in FIG. 14. When adhesively joined, it is important that the adhesive not be applied in the region of tab formation. In other words, it is desirable that the absorbent core material not be adhered to the backsheet in the region of tab formation, particularly if the amount of absorbent material in interior portion 54 of tab 52 is to be minimized.

Apparatus 120 comprises a female forming member 122, shown in FIG. 14 as a rotary female forming member having a plurality of void areas, or pockets, such as elongated pocket openings 208 in registered spaced apart relationship; a compression member 204, shown in FIG. 14 as a flexible belt compression member having a plurality of elongated slots 216 in registered spaced apart relationship; and a male forming member 124, such as a rotary male forming member, shown in FIG. 14 having a plurality of forming protrusions 212 in registered spaced apart relationship. The "registered spaced apart relationship" of the various components refers to the relative position of the operative components, such that the spaced apart components are in registry and coincide in operative relationship at forming nip 140 to form tab 52. The number of elongated pocket openings 208, slots 216 and forming protrusions 212 is not critical, and only need be at least one. However, a plurality, such as six, as shown, can significantly increase production rates in a commercially viable process.

In FIG. 14, the female forming member 122 is shown as an upper roll component, and the male forming member 124 is shown as a lower roll. However, as depicted here and herein, "upper" and "lower" positions are descriptive of the orientation as shown in FIG. 14, but otherwise are relative, and the elements described herein may be reversed in relative position or otherwise oriented differently with no practical effect.

As backsheet material 130 is moved in the machine direction (MD) shown in FIG. 14, it enters compression region 142 formed by the pressure of flexible compression belt 204 being disposed in a partially wrapped tensioned arrangement on female forming member 122. The extent of compression region 142 is determined by the wrap angle A1, and can thus be adjusted as necessary. In general, it is desirable that the wrap angle A1 be at least sufficient to define an arc length of at least one-half the machine direction dimension of absorbent core material 44 and more preferably at least the entire machine direction dimension of absorbent core material 44.

Compression belt 204 can be characterized as a two pulley system comprising male forming member 124 as one pulley, which may be driven about its axis of rotation, and pulley 126, which can be an adjustable idler roller. The amount of pressure exerted in compression region 142, as well as the wrap angle Al can be adjusted as necessary by adjusting the position of belt roller or pulley 126. In general, a more tensioned flexible belt 204 provides for higher compression in compression region 142.

As the backsheet material 130 and spaced apart absorbent core material 44 enters nip 140 under compressive forces, they are in operative registry with corresponding void areas 208 and forming protrusions 212. Additionally, flexible belt 204 is slotted, such that prior to, and at the nip 140, protrusion 212 extends through a corresponding slot 216, such that during formation of the tab 52 by the rotary former shown, a void area 208, a flexible slot 216, and a forming protrusion 212 are in operative, aligned, registered relationship, such that upon continued rotation of rotary male forming member 124 and rotary female forming member 122 a protrusion 212 contacts and strains backsheet material as it is received into a void area 208. The strain induced extension of the backsheet material causes plastic deformation of the material, thereby producing a tab 52.

Rotary forming members 122, and 124 can be formed of any suitable material, but general machine metals, for example steel, are preferred. Each rotary forming member may comprise multiple components. For example, in one embodiment, protrusions 212 are formed as separate members and joined to the rotary member in ways known in the art. For example, a thin plate can be machined in to a generally circular configuration having formed therein on the circumference thereof rotary forming members, with protrusions or voids machined integrally with the plate. The plate thus formed can then be "sandwiched" between two additional plates to form the male (if protrusions formed) or female (if voids formed) rotary forming members. The width of rotary forming members and compression belt should be generally the same, and at least as wide as the incoming web 130 of backsheet material. In FIG. 14 void pockets 208 are shown as the same general shape as protrusions 212, but they need not be so shaped. In practice, generally rectangular-shaped pockets are sufficient, and the depth of the void area is not critical. In fact, it is contemplated that a continuous void, i.e., a groove of sufficient depth being disposed about the circumference of rotary forming member 212, would suffice as the void area in forming member 122.

Flexible belt compression member 204 can be made of any material suitable for tensioned, flexible belts, such as timing belts. Flexible belt 204 preferably has a relatively smooth side facing the backsheet and absorbent core material. Slots 216 can be formed in flexible belt 204 by methods known in the art, such as by die cutting, shearing, or slitting. The longitudinal dimension D1 of slot 216 as well as the width oft the slot must be sufficient to allow protrusion 212 to extend through belt 204 in the nip 140 area during rotation of the rotary forming members.

The orientation and dimensions of the described components and parts can he adjusted, modified, and otherwise altered to meet the design requirements of the finished product. For example, the extended length of protrusion 212, and the depth of its corresponding female void area 208 need only be sufficient to produce the tab length desired, taking into account the thickness of belt 204 and the amount of strain recovery exhibited by certain strained and plastically deformed materials.

Other modifications are contemplated as having utility. For example, either or both of forming members 122 and 124 can be heated, or have heated regions, to aid in tab formation. Also, the protrusions 212 shown in FIG. 14, and depicted herein as generally flattened, rounded off elements (see, e.g., FIG. 12), can be of various shapes, including non-symmetrical shapes. Further, for a more commercially viable production process, multiple rotary forming members 122 and 124 can be "ganged" or set up in parallel to form multiple lines of tabs being formed simultaneously.

Once formed by hand or by a method and apparatus of the present invention, it has been found that it is beneficial to press the interlabial device in a folded configuration, as shown in FIG. 9. Pressing the interlabial device in a folded configuration can reduce the folded thickness of a relatively thick device, allowing more absorbent material to be provided in a space that will conveniently fit in the user's interlabial space. For example, for a device having a thickness $T_1$ as shown in FIG. 2, pressing a sufficient amount in a folded configuration allows the folded thickness to be less than $2 \times T_1$. In a preferred embodiment, the folded thickness of the product is about 4 to 6 mm, more preferably about 5 mm. In addition to permitting easier and more comfortable fit, the relatively smaller folded thickness dimension permits more economical and practical packaging, as shown in FIGS. 8 and 9. It should be understood that the features and components described herein may also be applied to other types of absorbent articles, including, but not limited to makeup removal pads, hard surface cleaning pads, diapers, sanitary napkins, tampons, incontinence devices and pantiliners. For example, the integral formed tab 52 as described herein can be very beneficial in forming gripping surfaces on backsheets of sanitary napkins, pantiliners, makeup removal pads, hard surface cleaning pads, and other disposable articles. Accordingly, the appended claims are intended to cover the features and components described herein as well as all combinations of features and components described herein.

TEST METHODS

Absorbent Capacity

Absorbent capacity may be determined as follows. The test is performed on samples that have been conditioned by leaving them in a room at 50% relative humidity and at 73° F. for a period of two hours prior to the test. The test should be performed under similar conditions.

The article is weighed to the nearest 0.1 gram. The article is then submerged in a beaker of sterile 0.9% saline solution (obtainable from the Baxter Travenol Company of Deerfield, Ill.), such that the article is totally submerged and is not bent or otherwise twisted or folded. The article is submerged for 10 minutes. The article is removed from the saline and laid horizontally on a wire mesh screen having square openings 0.25 inches by 0.25 inches (0.64 cm by 0.64 cm) for five minutes to allow the saline to drain out to the article. Both sides of the article are then covered with absorbent blotters, such as the filter paper #631 available from the Filtration Science Corp., Eaton-Dikeman Division of Mount Holly Springs, Penn. A uniform 1 pound per square inch (6.9 Pa) load is placed over the article to squeeze excess fluid out.

The absorbent blotters are replaced every 30 seconds until the amount of fluid transferred to the absorbent blotters is less than 0.5 grams in a 30 second period. Next, the article is weighed to the nearest 0.01 gram and the dry weight of the article is subtracted. The difference in grams is the absorbent capacity of the article.

| Water Dispersion Test | |
|---|---|
| Apparatus | |
| Shaker | Junior Orbit Shaker available from Lab Line Instruments of Melrose Park, Illinois. |
| Thermometer | 30 to 120° F. with 1 degree divisions |
| Timer | Digital stopwatch |
| Jar with Lid | 16 oz. glass jar with lid. |
| Conditioned Room | Temperature and humidity should be controlled to remain within the following limits: Temperature: 73 ± 3° F. (23° C. ± 2° C.) Humidity: 50 ± 2% Relative Humidity |

Test Setup
1. Fill the glass jar with 300 ml. of 73±3° F. tap water.
2. Set the speed on the Junior Orbit Shaker to 250 rpm according to the manufacturer's directions.

Procedure
1. Hold a sample (e.g. an absorbent interlabial device 20) 3 to 4 inches (7.6 to 10.2 centimeters) above the surface of the water in the jar. Gently drop the sample onto the water surface.
2. Place the lid on the jar.
3. Place the jar into the Junior Orbit Shaker such that the jar is oriented on its side.
4. Start the Junior Orbit shaker with the on/off switch, starting the timer when the shaker is turned on.
5. Record the time required until the sample separates into at least two pieces. Separation does not include the disassociation of a few individual fibers from an otherwise intact sample. The time is the total time the sample is being shaken.
6. Repeat steps 1 through 5 with three additional samples.

Calculation and Report and Calculate
Calculate and report the mean and standard deviation of the water dispersibility time for the four samples tested.

Flushability Test

Overview

As noted above, the terms "flushable or flushability" refer to a product's capacity to pass through typical commercially available household toilets and plumbing drainage systems without causing clogging or similar problems that can be directly associated with the physical characteristics of the product. For the purpose of the appended claims, the products are evaluated for flushability via relative ease of toilet bowl and trap evacuation and subsequent transport through a simulated plumbing system. The flushability of such a device should be measured by the following test procedure. The test procedure is designed to simulate two days of normal toilet usage for a family of 4 (2 men, 2 women). The test employs a flushing sequence to simulate the following conditions: male urination visits, female urination visits (including post urinary drying with tissue), disposal of the product (that is, the interlabial device or other device to be tested) with cleaning using tissue, and bowel movement visits. The amount of tissue to be used for each tissue flush is a normal loading of 2 strips of seven sheets. The normal loading is based on consumer research regarding typical habits and practices. The test is designed to simulate the conditions a product will encounter if it is flushed through a conventional toilet and into a municipal sewer or into a septic tank. Samples are evaluated for: 1) toilet bowl and trap clearance, 2) drain line blockage, and 3) disintegration during flushing.

Apparatus

Figure 10:
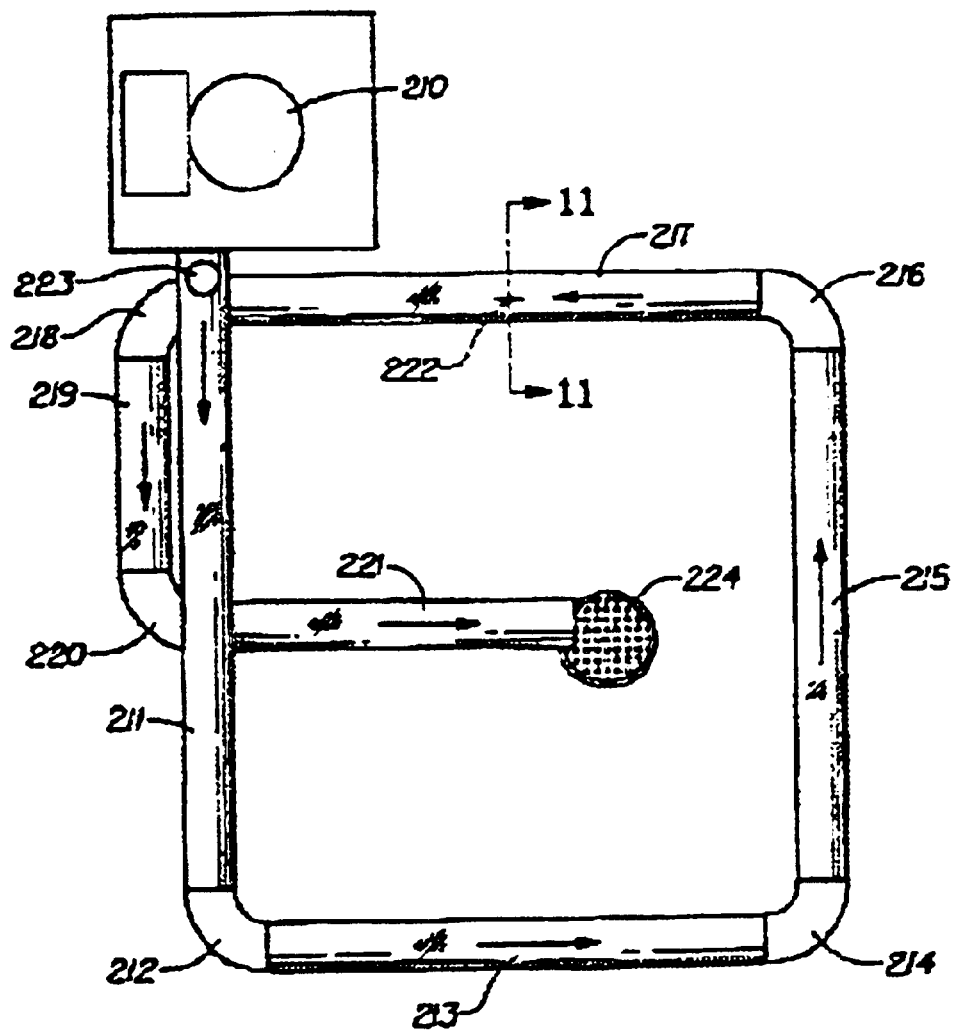
FIG. 10 is a plan view of an apparatus suitable for flushability determination according to the method described in the TEST METHODS section, below.
Figure 11:
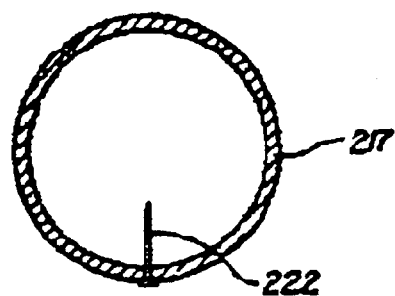
FIG. 11 is a cross-section of the flushability apparatus of FIG. 10 taken along line 11—11 thereof.

An apparatus suitable for the flushability test is shown in plan view in FIG. 10. The apparatus includes:
- a 3.5 gallon (13.2 liter) water saver siphon vortex toilet referred to as 210 (additional toilets can also be attached to the piping layout shown in FIG. 10 to evaluate the behavior of test samples using different flushing mechanisms such as commercial, pressure toilets);
- approximately 59 feet (18 meters) of 4 inch (10 cm) inside diameter acrylic pipe (As can be seen from FIG. 10, the piping is assembled in roughly a square configuration having linear runs 211, 213, 215, 217, 219, 221 approximately 10 feet (3 meters) long);
- a cast iron tee 223 slightly downstream of the toilet 210 that is open to the atmosphere for venting;
- five cast iron ninety degree elbows 212, 214, 216, 218, and 220;
- a snag 222 positioned vertically (FIG. 11) approximately 15 feet from the pipe's terminal end and approximately 1 inch (2.5 cm) long; and
- a screen (No. 4 Tyler sieve) to capture solid effluent for evaluation of disintegration.

The apparatus used for this method is set up to be equivalent to ANSI Standard A112.19.2M-1990 for Vitreous China fixtures. The piping is plumbed to provide a drop of 0.25 inch per foot (2 centimeters/meter) of pipe length.

Materials

Tissue Product used in Test: standard "CHARMIN" toilet tissue manufactured by The Procter & Gamble Company of Cincinnati, Ohio.

Synthetic Fecal Material: Prepared according to the method described below

Test Flushing Sequence

The test flushing sequence simulates 2 days of normal toilet usage for a family of 4 (2 men, 2 women; based on consumer habits and practices research). The sequence of 34 total flushes consists of 14 flushes with an empty bowl, 8 flushes with tissue only, 6 flushes with tissue and the product to be tested and 6 flushes with tissue and simulated fecal matter (SFM). When it is used, the SFM is placed in the bowl just prior to the addition of tissue. The SFM loading of 160 g ±5 g consists of two 1 inch (2.5 centimeter)×4 inch (10 centimeter) pieces and one 1 inch (2.5 centimeter)×2 inch (5 centimeter) piece. Folded tissue strips (or the catamenial product) are placed in the bowl at 10 second intervals. Ten seconds after the final strip or product is placed into the bowl, the toilet is flushed. The flushing sequence is described below as a series of two routines combined in the following order:

Routine #1 (To be performed first 6 times for a total of 30 flushes)
1) Flush With Tissue Only—Take a drain line blockage reading 2 minutes after the water reaches the simulated obstruction, wait 1 additional minute, and move to step 2.
2) Flush With Empty Bowl. Take a drain line blockage reading 2 minutes after the water reaches the snag point and move to step 3.
3) Flush With Tissue and Product—Take a drain line blockage reading 2 minutes after the water reaches the snag point, wait 1 additional minute, and move to step 4.

4) Flush With Empty Bowl. Take a drain line blockage reading 2 minutes after the water reaches the snag point and move to step 5.

5) Flush With Tissue and Simulated Fecal Matter (SFM). Take a drain line blockage reading 2 minutes after the water reaches the snag point, wait 1 additional minute.

Routine #2 (To be performed 1 time)

1) Flush With Tissue Only—Take a drain line blockage reading 2 minutes after the water reaches the snag point, wait 1 additional minute, and move to step 2.

2) Flush With Empty Bowl. Take a drain line blockage reading 2 minutes after the water reaches the snag point and move to step 3.

3) Flush With Tissue Only—Take a drain line blockage reading 2 minutes after the water reaches the snag point, wait 1 additional minute, and move to step 4.

4) Flush With Empty Bowl. Take a drain line blockage reading 2 minutes after the water reaches the snag point.

Total number of flushes per sequence is 34.

If, after the second flush in the flushing sequence, the product remains in the bowl or trap after flushing, the tissue and or product is plunged into the drainage line manually and the flushing sequence will continue. After completion of each trial loading, the drainage pipe will be cleared prior to beginning subsequent testing.

The above described flushing sequence is repeated three times for each test product.

Data Reporting

The degree of drain line blockage is determined by measuring the length of water dammed up behind the obstruction. Graduations are marked every 12 inches (30 centimeters) on the drainpipe upstream of the obstruction. Each one foot length that the water is backed up corresponds to 0.25 inch (0.6 centimeter) or 6.25% of blockage at the obstruction point. Test product residues which exit the drainpipe are also collected.

The following data are recorded for each evaluation:

1) Incidence of failure (%) of the product to clear bowl and trap in one flush

2) Incidence of failure (%) of the product to clear bowl and trap in two flushes 3) Incidence of product on simulated snag 4) Maximum level (%) of drain line blockage 5) Cumulative level (%) of drain line blockage over the 2 day simulated test period.

Preferably, the products described herein will completely clear the bowl at least about 70% of the time in two or fewer flushes, more preferably at least about 80% of the time in one flush, even more preferably at least about 90% of the time in one flush, and most preferably at least about 95% of the time in one flush. The products described herein will preferably have a maximum level of drain line blockage of less than or equal to about 80%. The products described herein will preferably have a cumulative level of drain line blockage over the 2 day simulated test period of less than or equal to about 50%.

Preparation of Synthetic Fecal Material

I. Materials Needed:

Feclone synthetic fecal matter (900 grams); (Available from Siliclone Studio, Valley Forge, Pa. as product BFPS-7 dry concentrate)

Tap water at 100° C. (6066 grams)

II. Equipment Needed:

Mixer (Available from Hobart Corp., Troy, Ohio as Model A200)

Extruder (Available from Hobart Corp., Troy, Ohio as Model 4812)

Disposable Centrifuge tubes with screw caps (50 ml) (Available from VWR Scientific, Chicago, Ill. as Catalog No. 21-008-176)

Water Bath to control temperature to 37° C.

III. Preparation:

1. Pour the 100° C. water into the mixing bowl of the mixer and add the dry Feclone concentrate.
2. Mix on low for 1 minute.
3. Mix on medium speed for 2 minutes.
4. After the material is well mixed, transfer to the extruder.
5. Using an ice pick, punch a small hole in the tip of each centrifuge tube.
6. Extrude the Feclone into the centrifuge tubes.
7. Cap the centrifuge tubes and store in the refrigerator.
8. Before using, put the tubes in the water bath at 38° C.

28 Day Sludge Test

Purpose:

To determine the extent to which an absorbent article disintegrates upon exposure to biologically active anaerobic sludge. Anaerobic conditions are typically found in household septic tanks, as well as in municipal sewage treatment facilities in the form of anaerobic sludge digesters. Test products, such as the absorbent article are combined with anaerobic digester sludge to determine the extent and rate of disintegration of test products over a 28 day period. Disintegration (as measured by weight change) is typically measured on days 3, 7 14, 21 and 28 of the particular study. This protocol is modeled after the National Sanitation Foundation, Ann Arbor, Mich., International Protocol: Evaluation of the Anaerobic Disintegration of a Test Product, November, 1992.

Materials:

Control Product

TAMPAX Regular brand tampons will be used as a positive control product in the anaerobic disintegration test.

Material Preparation

Prior to the addition of the test and control products to the reactors, the materials will be dried in a hot air oven at 103°±2° C. for 2 hours and then weighed to determine the initial weight. Approximately equal weights of the control and the test products will be placed in respective reactors.

Anaerobic sludge:

The sludge used in this evaluation will be anaerobic sludge obtained from a municipal waste water treatment plant, or raw sewage obtained as influent from a waste water treatment plant that has been concentrated by settling and decanting the overlying water. Prior to use in the evaluation, the following parameters of the sludge will be measured in accordance with standard laboratory operating procedures:

Total solids

Total volatile solids pH

The sludge should meet the following criteria for use in the evaluation:

pH between 6.5 and 8.

Total solids ≧15,000 mg/L

Total volatile solids ≧10,000 mg/L

The criteria for the activity of the sludge requires that the control tampon material must lose at least 95% of its initial dry weight after 28 days exposure.

Procedure:

The test and control products are added to a 2L wide mouth glass flask (reactor) containing 1500 ml of anaerobic digester sludge or concentrated raw sewage. Three reactor flasks per test material per sampling day are prepared. Thus, if disintegration is measured on days 3, 7, 14, 21, and 28, there will be a total of 15 reactor flasks for the test product and 15 flasks for the control product. The reactors are sealed and placed in an incubator maintained at 35±2° C. On the specified sampling days, three reactors each for the test and control material are removed from the incubator. On the designated sample days, the contents of each reactor will be passed through a 1 mm mesh screen to recover any undisintegrated material. Any collected material will be rinsed with tap water, removed from the screen and placed in a hot air oven at 103±2° C. for at least 2 hours. The dried material will be weighed to determine final weight. Visual observations of the physical appearance of the materials when recovered from the reactors will also be made and recorded.

Results:

The rate and extent of anaerobic disintegration of each test material and the control material is determined from initial dry weights of the material and the dried weights of the material recovered on the sampling days. The percent anaerobic disintegration is determined using the following equation (percent weight loss):

$$\text{Percent Disintigration} = \frac{(\text{initial dry weight} - \text{final dry weight})}{(\text{initial dry weight})} \times 100$$

The average percent disintegration for the test and control products for each sampling day will be presented. For the purposes of the appended claims, the percent disintegration values are for day 28 of the study.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention.

What is claimed is:

1. An absorbent device insertable into the interlabial space of a female wearer, said absorbent device having a length, a width, a thickness, and a longitudinal centerline, said absorbent device comprising a backsheet having an integral protrusion formed by strain induced plastic deformation, said protrusion being of sufficient dimensions to aid in insertion into the interlabial space.

2. The absorbent device of claim 1 wherein said protrusion is formed near the longitudinal centerline.

3. The absorbent device of claim 1 wherein said protrusion comprises an interior portion.

4. The absorbent device of claim 3 wherein said absorbent device comprises absorbent material in said interior portion of said protrusion.

5. The absorbent device of claim 4 wherein said absorbent material comprises absorbent gelling material.

* * * * *